United States Patent [19]

Magnusson et al.

[11] Patent Number: 5,474,986
[45] Date of Patent: Dec. 12, 1995

[54] METHOD FOR TREATING GALABIOSE-BINDING BACTERIA INFECTIONS

[75] Inventors: Hans G. Magnusson, Lund; Jan O. Kihlberg, Malmö, both of Sweden

[73] Assignee: Symbicom Aktiebolag, Umea, Sweden

[21] Appl. No.: 689,077

[22] PCT Filed: Aug. 11, 1989

[86] PCT No.: PCT/DK89/00192

§ 371 Date: Apr. 11, 1991

§ 102(e) Date: Apr. 11, 1991

[87] PCT Pub. No.: WO90/01488

PCT Pub. Date: Feb. 22, 1990

[30] Foreign Application Priority Data

Aug. 12, 1988 [DK] Denmark .................. 4550/88

[51] Int. Cl.⁶ .................. A61K 31/70; C07H 3/04
[52] U.S. Cl. .................. 514/53; 435/7.37
[58] Field of Search .................. 536/1.1, 4.1; 435/7.37, 435/7.21; 514/53

[56] References Cited

U.S. PATENT DOCUMENTS

| | | | |
|---|---|---|---|
| 4,657,849 | 4/1987 | Kallenius et al. | 435/7 |
| 4,675,392 | 6/1987 | Dahmen et al. | 536/17.6 |

FOREIGN PATENT DOCUMENTS

| | | |
|---|---|---|
| 0089940 | 9/1983 | European Pat. Off. . |
| 0132242 | 1/1985 | European Pat. Off. . |
| WO8102520 | 9/1981 | WIPO . |
| WO8604065 | 7/1986 | WIPO . |
| WO8604064 | 7/1986 | WIPO . |

OTHER PUBLICATIONS

Carbohydrate Research, 152, 113–130, Kehlberg et al. (1986).

Primary Examiner—Douglas W. Robinson
Assistant Examiner—Gary L. Kunz
Attorney, Agent, or Firm—Iver P. Cooper

[57] ABSTRACT

A method for treating infections caused by galabiose-binding bacteria using galabiose derivatives modified at the 3' and anomeric positions. The galabiose-derivatives and compositions of same are also disclosed.

31 Claims, No Drawings

METHOD FOR TREATING GALABIOSE-BINDING BACTERIA INFECTIONS

BACKGROUND OF THE INVENTION

1. Field of the Invention

The present invention relates to novel synthetic analogues of galabiosides useful as i.a. synthetic biological receptors.

2. Description of the Prior Art

Adhesion to cell-surface carbohydrates is considered to be important for bacterial growth and possibly for the expression of pathogenicity and is mediated via proteinaceous appendages termed pill or fimbriae. Also, glycolipids, glycoproteins and simple glycosides have been shown to function as specific biological receptors towards lectins and antibodies. The specificity and strength of the binding depends on the presence of both hydrophilic (e.g. hydroxyl groups) and hydrophobic (e.g. CH-groups) areas in the sugar molecule.

In order to investigate possible affinity differences, applicants have prepared and investigated a number of glycosides of galabiose and investigated their properties as inhibitors. Thus, a series of galabioside analogues were prepared and used as inhibitors of the agglutination of human red blood cells by genetically well-defined bacteria, namely mutants (HB101/pPAP5) of uropathogenic E.coli which carries galabiose-specific adhesin but is void of other sugar-binding adhesins in the pill, the mutants therefore being used as a standardized model of the wild strain.

The investigations indicated that any alterations of most of the hydroxy groups (e.g. removal of the hydroxy group, replacement thereof with atoms such as fluorine, substitution thereof to form e.g. alkoxy groups) resulted in a drastic reduction or complete removal of the ability of the glycoside to inhibit agglutination of red blood cells by means of the above-mentioned uropathogenic E.coli mutants. It was concluded that the positions in which the alterations had these negative effects were in some way involved either in essential hydrogen bonding interactions (either H-donating or H-accepting) with the bacterial adhesin or were involved in intra-molecular hydrogen bonding.

However, the investigations revealed that alterations in the 3' position (meaning the 3-position of the non-reducing galacross unit) could result in increased inhibitor activity. Also, alterations in the nature of the aglycon moiety towards higher lipophilicity resulted in increased inhibitor activity.

SUMMARY OF THE INVENTION

Based on the above outlined observations, the present invention concerns compound of the general formula I

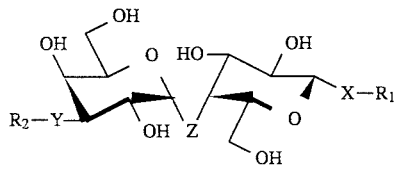

I wherein $R_1$ is $C_{1-24}$ alkyl; $C_{2-24}$ alkenyl; $C_{2-24}$ alkynyl; tri($C_{1-4}$ alkyl)silylethyl; aryl optionally substituted with hydroxy, amino, $C_{1-4}$ alkyl, $C_{1-4}$ alkoxy, nitro, halogen, or phenoxy; mono- or di-halogen-$C_{1-4}$alkyl; phenyl-$C_{1-4}$alkyl;

a group of the formula II or IIa $$R_3-(CH_2)_n-S(O)_m-CH_2CH_2-\qquad\text{II}$$

$$(R_3-(CH_2)_n-S(O)_m-CH_2)_2CH-CH_2-\qquad\text{IIa}$$

wherein $R_3$ is H, carboxy, carboxy-$C_{1-4}$ alkyl, hydroxy, amino, or a carrier, n is an integer from 1 to 24, and m is 0 or 2;

a group of the formula III or IIIa $$Phe-S(O)_m-CH_2CH_2-\qquad\text{III}$$

$$(Phe-S(O)_m-CH_2)_2CH-CH_2-\qquad\text{IIIa}$$

wherein m is as defined above, and each Phe is a phenyl group optionally monosubstituted with hydroxy, amino, $C_{1-4}$ alkyl, $C_{1-4}$ alkoxy, nitro, halogen, or phenoxy a group of the formula IV $$R_4CH_2CH(CH_2R_5)CH_2-\qquad\text{IV}$$

wherein $R_4$ and $R_5$ independently are halogen a group $Q-(CH_2)_n-$ where Q is a carrier, and n is as defined above; and $R_2$ is a mono- or disaccharide moiety connected via a glycosidic bond; $C_{1-18}$ alkyl; $C_{2-18}$ alkenyl; $C_{2-18}$ alkynyl; $C_{1-18}$ alkyloxymethyl; $C_{1-18}$ alkanoyl; α-hydroxy-$C_{1-18}$ alkanoyl; naphthyl-, heterocyclyl- or phenyl-$C_{1-8}$ alkoxy where the naphthyl, heterocyclyl or phenyl group may be substituted with hydroxy, amino, $C_{1-4}$ alkyl, $C_{1-4}$ alkoxy, nitro, halogen, or phenoxy; tri($C_{1-4}$-alkyl)silylethyl; tri($C_{1-4}$-alkyl)silyl; tri($C_{1-4}$-alkyl)silylethoxymethyl; halogen; ω-hydroxy-$C_{1-4}$alkyl; tetrahydropyranyl; benzyloxymethyl; $C_{3-8}$ cycloalkyl, a monoterpenyl moiety; benzoyl optionally monosubstituted with hydroxy, amino, $C_{1-4}$ alkyl, $C_{1-4}$ alkoxy, nitro, halogen, or phenoxy; the acyl residue of a naturally occurring amino acid; or a group of the formula V $$R_6-C(O)-N(R_7)-(CH(R_8)-CH_2-\qquad\text{V}$$

wherein $R_6$ is $C_{1-4}$ alkyl; or phenyl optionally monosubstituted with hydroxy, amino, $C_{1-4}$ alkyl, $C_{1-4}$ alkoxy, nitro halogen, or phenoxy, $R_7$ is H or $C_{1-4}$ alkyl, and $R_8$ is H, $C_{1-4}$ alkyl, or hydroxy-$C_{1-4}$ alkyl, Z is $-O-$, $-S-$, $-SO_2-$, or $-CH_2-$, X is $-O-$, $-S-$, $-SO_2-$, $-CH_2-$, or $-NR_3-$, wherein $R_3$ is H or is one of the meanings for $R_2$ above, and $R_3$ and $R_1$ optionally being connected to form a ring, and Y is $-O-$ or $-NR_3-$ where $R_3$ is as defined above, $R_3$ and $R_2$ optionally being connected to form a ring.

Since compounds of the formula I exhibit increased inhibiting activity towards the adhesion of bacteria to receptors on tissue surfaces, a further aspect of the invention is pharmaceutical compositions comprising a compound of the general formula I as defined above and a pharmaceutically acceptable carrier that is inert with respect to bacteria/receptor interactions.

Yet another aspect of the invention is a diagnostic kit which incorporates one or more compounds of the general formula I, the kit being useful in the detection of the presence of bacteria in samples of e.g. body fluids such as urine, in particular the detection of uropathogenic E.coli strains.

Yet another aspect of the present invention is the compounds of the general formula I for use in therapy or prophylaxis of bacterial infections, in particular uropathogenic E.coli infections.

Yet another aspect of the invention is a method of detecting the presence of bacteria, in particular uropathogenic E.coli in a liquid sample comprising bringing the sample into contact with a compound of the general formula I followed by detection of bacteria that have adhered to the compounds of the formula I.

In yet another aspect, the invention concerns use of the compounds of the general formula I for the preparation of a pharmaceutical composition useful in therapy or prophylaxis of bacterial infections, in particular uropathogenic E.coli infections, as well as a method for treating or preventing bacterial infections, in particular uropathogenic E.coli infections, said method comprising administering to a patient in need thereof a compound of the formula I or a pharmaceutical composition comprising a compound of the formula I.

DETAILED DESCRIPTION OF THE INVENTION

In the present context, the terms "$C_{1-4}$alkyl" and "$C_{1-24}$alkyl" designates alkyl groups with 1–4 or 1–24 carbon atoms which may be straight, branched or cyclic such as methyl, ethyl, propyl, isopropyl, butyl, isobutyl, tert.butyl, cyclohexyl, hexyl, octyl, dodecyl, hexadecyl, octadecyl, etc. The term "$C_{2-24}$alkenyl" designates monounsaturated alkyl groups with 2–24 carbon atoms which may be straight or branched, preferably straight, in which the double bond may be present anywhere in the chain, for example vinyl, 1-propenyl, 2-propenyl, hexenyl, decenyl, hexadecenyl, octadecenyl. The term "$C_{2-24}$alkynyl" designates a alkyl group with 2–24 carbon atoms and incorporating a triple bond, e.g. ethynyl, 1-propenyl, 2-propenyl, 2-butynyl etc. The term "halogen" designates Cl, Br, I and F, preferably Cl and Br.

A mono- or di-halogen-$C_{1-4}$alkyl group may be substituted in any position and if substituted with 2 halogen atoms, the halogen atoms may be the same or different.

The term "carrier" for Q designates any organic or inorganic, polymeric or macromolecular structure to which the aglycon part of the O-glycosidic compound of the formula I is attached either covalently or by e.g. hydrophobic interaction. Examples of such carriers are residues of proteins, polysaccharides, plastic polymers and inorganic materials. Residues of proteins are preferably bonded through nucleophilic groups in the proteins, e.g. such groups as amino, hydroxy and mercapto groups. The proteins themselves may be any of a wide variety of proteins, in particular biologically compatible proteins such as globulins, albumins such as bovine serum albumin, fibrins, polylysin, "key-hole" limpet haemocyanine (KLH), etc. The polysaccharides, to which the O-glycosidic compounds are attached, may be any of a wide variety of polysaccharides. The aglycon part of the compound of formula I may be bonded through hydroxy groups on ordinary polysaccharides such as cellulose, starch or glycogen, through amino groups on amino saccharides such as chitosane or aminated sepharose, and through mercapto groups of thio-modified polysaccharides. Examples of plastics to which the aglycon part of the compounds of the formula I may be attached are aminated latex, thiolated, aminated, or hydroxylated polystyrene, and polyvinyl alcohol. The plastics in question may be in the form of e.g. beads or film. Examples of inorganic material, to which the aglycon part of the compounds of the formula I may be attached are silicon oxide materials such as silica gel, zeolite, diatomaceous earth, or the surface of various glass or silica gel types such as thiolated or aminated glass, where the silica gel or the glass may be in the form of e.g. beads. Another example of an inorganic material is aluminium oxide.

The term "mono- or disaccharide moiety" for $R_2$ can be any naturally occurring monosaccharide or disaccharide consisting of two such monosaccharide units, the monosaccharide units being selected from D-glycosamine, D-galactosamine, D-glucose, D-mannose, D-galactose, D-gulose, D-ribose, D-arabinose, D-fructose etc.

The term "$C_{1-18}$alkanoyl" designates the acyl residue of a alkanoic acid derived from a $C_{1-18}$alkane in keeping with the above definition of $C_{1-2}$alkyl, for example acetyl, propionyl, butanoyl, hexanoyl, octanoyl, dodecanoyl, hexadecanoyl, octadecanoyl etc.

The term "heterocyclyl" designates single or fused, 5- or 6-membered aromatic heterocyclic groups containing one to four hetero atoms selected from O, S and N, e.g. 2-, 3- or 4-pyridinyl, 2- or 3-thienyl, 2-, 4- or 5-thiazolyl, 2-, 4- or 5-oxazolyl, 2-imidazolyl, 5-isoxazolyl, 5-isothiazolyl, 2-furanyl, 2- or 5-pyrimidinyl, 5-[1,3]-oxazinyl, or 5-[1,3]-thiazinyl.

The term "acyl residue of a naturally occurring amino acid" designates the acyl residue of the D-amino acids occurring in proteins in nature, e.g. alanoyl, valoyl, leucoyl, isoleucoyl, prolinoyl, phenylalanoyl, tryptophanoyl, methionoyl, glycoyl, seroyl, threonyol, cysteinoyl, tyrosoyl, asparagoyl, glutamoyl, lysoyl, arginoyl, histidoyl and the acyl residues of aspartic acid and glutamic acid, the acyl residue referring both to the carboxy group next to the amino function as well as the carboxy group at the end of the respective side chains, preferably, however, the carboxy groups next to the amino functions.

In the compounds of formula I, it is preferred that Z is —O—.

In another embodiment, it is preferred that Y is —O—.

In a further embodiment, it is preferred that X is —O— or —S—, in particular —S—.

Other preferred compounds are those in which $R_2$ and Y together is $(C_{1-8}alkyl)_2N$— where the two $C_{1-8}$ alkyl groups optionally are connected to form a ring, such as tetrahydropyridtnyl.

Other preferred compounds are those in which $R_1$ is $C_{1-24}$ alkyl; tri($C_{1-4}$ alkyl)silylethyl; aryl optionally substituted with amino or nitro; a group of the formula II or IIa wherein $R_3$ is H, carboxy, carboxy-$C_{1-4}$ alkyl, or a carrier, and n and m are as defined; a group of the formula III or IIIa wherein m is as defined, and each phenyl group optionally is monosubstituted with amino or nitro; or a group Q—$(CH_2)_n$— where Q is a carrier and n is as defined above.

In yet another preferred embodiment, $R_2$ is a mono- or disaccharide moiety connected via a glycosidic bond; $C_{1-18}$ alkyl; $C_{1-18}$ alkyloxymethyl; tetrahydropyranyl; or benzyloxymethyl.

Particularly preferred compounds are compounds in which $R_2$ is a 2-acetamido-2-deoxy-β-D-galactopyranosyl residue; a 2-deoxy-2-phthalamido-β-D-galactopyranosyl residue; $C_{1-6}$ alkyl; $C_{1-6}$ alkyloxymethyl; tetrahydropyranyl; or benzyloxymethyl.

Other types of preferred compounds are dimeric compounds that contain a galabiose moiety at each end of a spacing chain. Examples of such compounds are those in which $R_2$—Y is OH, $CH_3O$—, $CH_3CH_2O$— or $(CH_3)_2CHO$—, and $R_1X$— is a bivalent chain of the formula —OCH$_2$CH$_2$S(CH$_2$)$_p$SCH$_2$CH$_2$O— where p is 1–12, preferably 3,6 or 9, the chain having a galabiose moiety modified in the 3'-position in the specified manner at each end. The compounds may be defined by the general formula VI:

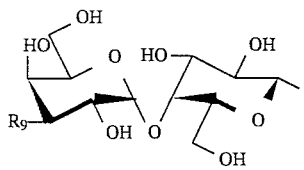
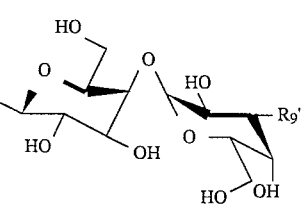

VI where $R_9$ and $R_9'$ independently are OH, CH$_3$O—, CH$_3$CH$_2$O— or (CH$_3$)$_2$CHO—, and p is an integer from 1 to 12, preferably 3, 6 or 9.

The advantage of such compounds is that they have provisions at each end of the molecule to engage in a adhesin reaction at the surface of bacteria. Thus, the molecule could block two adhesin sites on the surface of the same bacterium thereby probably increasing the binding coefficient drastically but could conceivably also bind two bacteria together, thereby aiding in immobilizing the bacteria.

Examples of preferred compounds of the invention are those mentioned below where the designation "galabiose" comprises the sugar residue in the following structure:

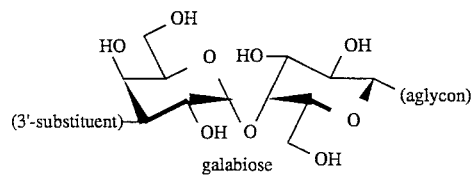

and where the group R$_2$Y— (the 3'-substituent) is the moiety to the left of the term "galabiose" and the moiety —XR$_1$ (the aglycon) is the moiety indicated to the right of the term "galabiose":

GalNAcβO-galabiose-O(CH$_2$)$_2$S(CH$_2$)$_2$COOCH$_3$
GalNAcβO-galabiose-O(CH$_2$)$_2$S(CH$_2$)$_{10}$COOCH$_3$
GalNAcβO-galabiose-O(CH$_2$)$_2$S(CH$_2$)$_{15}$CH$_3$
GalNAcβO-galabiose-OCH$_2$CH[CH$_2$S(CH$_2$)$_{15}$CH$_3$]$_2$
GalNAcβO-galabiose-OCH$_2$CH[CH$_2$SO$_2$(CH$_2$)$_{15}$CH$_3$]$_2$
GalNAcβO-galabiose-OCH$_2$CH[CH$_2$SO$_2$(CH$_2$)$_7$CH$_3$]
    CH$_2$SO$_2$(CH$_2$)$_{10}$COOCH$_3$
GalNAcβO-galabiose-OPh-p-NH$_2$
GalNAcβO-galabiose-O(CH$_2$)$_2$SPh-p-NH$_2$
GalNAcβO-galabiose-S(CH$_2$)$_{10}$COOCH$_3$
GalNAcβO-galabiose-OCH$_3$
GalNAcβO-galabiose-OCH$_2$CH$_3$
GalNAcβO-galabiose-OCH$_2$CH(CH$_3$)$_2$
GalNAcβO-galabiose-O(CH$_2$)$_2$Si(CH$_3$)$_3$
GalNAcβO-galabiose-O(CH$_2$)$_2$S(CH$_2$)$_{10}$CO-BSA
GalNAcβO-galabiose-O(CH$_2$)$_2$S(CH$_2$)$_{10}$CO-KLH
GalNAcβO-galabiose-O(CH$_2$)$_2$S(CH$_2$)$_{10}$CO-Latex
GalNAcβO-galabiose-O(CH$_2$)$_2$S(CH$_2$)$_{10}$CO-Glass
GalNAcβO-galabiose-O(CH$_2$)$_2$S(CH$_2$)$_{10}$CO-Silica gel
GalNAcβO-galabiose-O(CH$_2$)$_2$S(CH$_2$)$_{10}$CO-Polystyrene
GalNAcβO-galabiose-O(CH$_2$)$_2$S(CH$_2$)$_{10}$CO-sepharose
GalNAcβO-galabiose-O(CH$_2$)$_2$S(CH$_2$)$_{10}$CO-dextran
GalNPhthβO-galabiose-O(CH$_2$)$_2$S(CH$_2$)$_2$COOCH$_3$
GalNPhthβO-galabiose-O(CH$_2$)$_2$S(CH$_2$)$_{10}$COOCH$_3$
GalNPhthβO-galabiose-O(CH$_2$)$_2$S(CH$_2$)$_{15}$CH$_3$
GalNPhthβO-galabiose-OCH$_2$CH[CH$_2$S(CH$_2$)$_{15}$CH$_3$]$_2$
GalNPhthβO-galabiose-OCH$_2$CH[CH$_2$SO$_2$(CH$_2$)$_{15}$CH$_3$]$_2$
GalNPhthβO-galabiose-OCH$_2$CH[CH$_2$SO$_2$(CH$_2$)$_7$CH$_3$]
    CH$_2$SO$_2$(CH$_2$)$_{10}$COOCH$_3$
GalNPhthβO-galabiose-OPh-p-NH$_2$
GalNPhthβO-galabiose-O(CH$_2$)$_2$SPh-P-NH$_2$
GalNPhthβO-galabiose-S(CH$_2$)$_{10}$COOCH$_3$
GalNPhthβO-galabiose-OCH$_3$
GalNPhthβO-galabiose-OCH$_2$CH$_3$
GalNPhthβO-galabiose-OCH$_2$CH(CH$_3$)$_2$
GalNPhthβO-galabiose-O(CH$_2$)$_2$Si(CH$_3$)$_3$
GalNPhthβO-galabiose-O(CH$_2$)$_2$S(CH$_2$)$_{10}$CO-BSA
GalNPhthβO-galabiose-O(CH$_2$)$_2$S(CH$_2$)$_{10}$CO-KLH
GalNPhthβO-galabiose-O(CH$_2$)$_2$S(CH$_2$)$_{10}$CO-Latex
GalNPhthβO-galabiose-O(CH$_2$)$_2$S(CH$_2$)$_{10}$CO-Glass
GalNpthβO-galabiose-O(CH$_2$)$_2$S(CH$_2$)$_{10}$CO-Silica gel
GalNPhthβO-galabiose-O(CH$_2$)$_2$S(CH$_2$)$_{10}$CO-Polystyrene
GalNPhthβO-galabiose-O(CH$_2$)$_2$S(CH$_2$)$_{10}$CO-sepharose
GalNPhthβO-galabiose-O(CH$_2$)$_2$S(CH$_2$)$_{10}$CO-dextran
GalαO-galabiose-O(CH$_2$)$_2$S(CH$_2$)$_2$COOCH$_3$
GalαO-galabiose-O(CH$_2$)$_2$S(CH$_2$)$_{10}$COOCH$_3$
GalαO-galabiose-O(CH$_2$)$_2$S(CH$_2$)$_{15}$CH$_3$
GalαO-galabiose-OCH$_2$CH[CH$_2$S(CH$_2$)$_{15}$CH$_3$]$_2$
GalαO-galabiose-OCH$_2$CH[CH$_2$SO$_2$(CH$_2$)$_{15}$CH$_3$]$_2$
GalαO-galabiose-OCH$_2$CH[CH$_2$SO$_2$(CH$_2$)$_7$CH$_3$]
    CH$_2$SO$_2$(CH$_2$)$_{10}$COOCH$_3$
GalαO-galabiose-OPh-p-NH$_2$
GalαO-galabiose-O(CH$_2$)$_2$SPh-p-NH$_2$
GalαO-galabiose-S(CH$_2$)$_{10}$COOCH$_3$
GalαO-galabiose-OCH$_3$
GalαO-galabiose-OCH$_2$CH$_3$
GalαO-galabiose-OCH$_2$CH(CH$_3$)$_2$
GalαO-galabiose-O(CH$_2$)$_2$Si(CH$_3$)$_3$
GalαO-galabiose-O(CH$_2$)$_2$S(CH$_2$)$_{10}$CO-BSA
GalαO-galabiose-O(CH$_2$)$_2$S(CH$_2$)$_{10}$CO-KLH
GalαO-galabiose-O(CH$_2$)$_2$S(CH$_2$)$_{10}$CO-Latex
GalαO-galabiose-O(CH$_2$)$_2$S(CH$_2$)$_{10}$CO-Glass
GalαO-galabiose-O(CH$_2$)$_2$S(CH$_2$)$_{10}$CO-Silica gel
GalαO-galabiose-O(CH$_2$)$_2$S(CH$_2$)$_{10}$CO-polystyrene
GalαO-galabiose-O(CH$_2$)$_2$S(CH$_2$)$_{10}$CO-sepharose
GalαO-galabiose-O(CH$_2$)$_2$S(CH$_2$)$_{10}$CO-dextran
CH$_3$O-galabiose-O(CH$_2$)$_2$S(CH$_2$)$_2$COOCH$_3$
CH$_3$O-galabiose-O(CH$_2$)$_2$S(CH$_2$)$_{10}$COOCH$_3$
CH$_3$O-galabiose-O(CH$_2$)$_2$S(CH$_2$)$_{15}$CH$_3$
CH$_3$O-galabiose-OCH$_2$CH[CH$_2$S(CH$_2$)$_{15}$CH$_3$]$_2$
CH$_3$O-galabiose-OCH$_2$CH[CH$_2$SO$_2$(CH$_2$)$_{15}$CH$_3$]$_2$
CH$_3$-galabiose-OCH$_2$CH[CH$_2$SO$_2$(CH$_2$)$_7$CH$_3$]
    CH$_2$SO$_2$(CH$_2$)$_{10}$COOCH$_3$
CH$_3$O-galabiose-OPh-p-NH$_2$
CH$_3$O-galabiose-O(CH$_2$)$_2$SPh-p-NH$_2$
CH$_3$O-galabiose-S(CH$_2$)$_{10}$COOCH$_3$
CH$_3$O-galabiose-OCH$_3$
CH$_3$O-galabiose-OCH$_2$CH$_3$
CH$_3$O-galabiose-OCH$_2$CH(CH$_3$)$_2$
CH$_3$O-galabiose-O(CH$_2$)$_2$Si(CH$_3$)$_3$
CH$_3$O-galabiose-O(CH$_2$)$_2$S(CH$_2$)$_{10}$CO-BSA
CH$_3$O-galabiose-O(CH$_2$)$_2$S(CH$_2$)$_{10}$CO-KLH CH₃O-galabiose-O(CH₂)₂S(CH₂)₁₀CO-Latex
CH₃O-galabiose-O(CH₂)₂S(CH₂)₁₀CO-Glass
CH₃O-galabiose-O(CH₂)₂S(CH₂)₁₀CO-Silica gel
CH₃O-galabiose-O(CH₂)₂S(CH₂)₁₀CO-polystyrene
CH₃O-galabiose-O(CH₂)₂S(CH₂)₁₀CO-sepharose
CH₃O-galabiose-O(CH₂)₂S(CH₂)₁₀CO-dextran
CH₃CH₂O-galabiose-O(CH₂)₂S(CH₂)₂COOCH₃
CH₃CH₂O-galabiose-O(CH₂)₂S(CH₂)₁₀COOCH₃
CH₃CH₂O-galabiose-O(CH₂)₂S(CH₂)₁₅CH₃
CH₃CH₂O-galabiose-OCH₂CH[CH₂S(CH₂)₁₅CH₃]₂
CH₃CH₂O-galabiose-OCH₂CH[CH₂SO₂(CH₂)₁₅CH₃]₂
CH₃CH₂O-galabiose-OCH₂CH[CH₂SO₂(CH₂)₇CH₃]CH₂SO₂(CH₂)₁₀COOCH₃
CH₃CH₂O-galabiose-OPh-p-NH₂
CH₃CH₂O-galabiose-O(CH₂)₂SPh-p-NH₂
CH₃CH₂O-galabiose-S(CH₂)₁₀COOCH₃
CH₃CH₂O-galabiose-OCH₃
CH₃CH₂O-galabiose-OCH₂CH₃
CH₃CH₂O-galabiose-OCH₂CH(CH₃)₂
CH₃CH₂O-galabiose-O(CH₂)₂Si(CH₃)₃
CH₃CH₂O-galabiose-O(CH₂)₂S(CH₂)₁₀CO-BSA
CH₃CH₂O-galabiose-O(CH₂)₂S(CH₂)₁₀CO-KLH
CH₃CH₂O-galabiose-O(CH₂)₂S(CH₂)₁₀CO-Latex
CH₃CH₂O-galabiose-O(CH₂)₂S(CH₂)₁₀CO-Glass
CH₃CH₂O-galabiose-O(CH₂)₂S(CH₂)₁₀CO-Silica gel
CH₃CH₂O-galabiose-O(CH₂)₂S(CH₂)₁₀CO-polystyrene
CH₃CH₂O-galabiose-O(CH₂)₂S(CH₂)₁₀CO-sepharose
CH₃CH₂O-galabiose-O(CH₂)₂S(CH₂)₁₀CO-dextran
(CH₃)₂CHO-galabiose-O(CH₂)₂S(CH₂)₂COOCH₃
(CH₃)₂CHO-galabiose-O(CH₂)₂S(CH₂)₁₀COOCH₃
(CH₃)₂CHO-galabiose-O(CH₂)₂S(CH₂)₁₅CH₃
(CH₃)₂CHO-galabiose-OCH₂CH[CH₂S(CH₂)₁₅CH₃]₂
(CH₃)₂CHO-galabiose-OCH₂CH[CH₂SO₂(CH₂)₁₅CH₃]₂
(CH₃)₂CHO-galabiose-OCH₂CH[CH₂SO₂(CH₂)₇CH₃]CH₂SO₂(CH₂)₁₀COOCH₃
(CH₃)₂CHO-galabiose-OPh-P-NH₂
(CH₃)₂CHO-galabiose-O(CH₂)₂SPh-P-NH₂
(CH₃)₂CHO-galabiose-S(CH₂)₁₀COOCH₃
(CH₃)₂CHO-galabiose-OCH₃
(CH₃)₂CHO-galabiose-OCH₂CH₃
(CH₃)₂CHO-galabiose-OCH₂CH(CH₃)₂
(CH₃)₂CHO-galabiose-O(CH₂)₂Si(CH₃)₃
(CH₃)₂CHO-galabiose-O(CH₂)₂S(CH₂)₁₀CO-BSA
(CH₃)₂CHO-galabiose-O(CH₂)₂S(CH₂)₁₀CO-KLH
(CH₃)₂CHO-galabiose-O(CH₂)₂S(CH₂)₁₀CO-Latex
(CH₃)₂CHO-galabiose-O(CH₂)₂S(CH₂)₁₀CO-Glass
(CH₃)₂CHO-galabiose-O(CH₂)₂S(CH₂)₁₀CO-Silica gel
(CH₃)₂CHO-galabiose-O(CH₂)₂S(CH₂)₁₀CO-polystyrene
(CH₃)₂CHO-galabiose-O(CH₂)₂S(CH₂)₁₀CO-sepharose
(CH₃)₂CHO-galabiose-O(CH₂)₂S(CH₂)₁₀CO-dextran
CH₂=CHCH₂O-galabiose-O(CH₂)₂S(CH₂)₂COOCH₃
CH₂=CHCH₂O-galabiose-O(CH₂)₂S(CH₂)₁₀COOCH₃
CH₂=CHCH₂O-galabiose-O(CH₂)₂S(CH₂)₁₅CH₃
CH₂=CHCH₂O-galabiose-OCH₂CH[CH₂S(CH₂)₁₅CH₃]₂
CH₂=CHCH₂O-galabiose-OCH₂CH[CH₂SO₂(CH₂)₁₅CH₃]₂
CH₂=CHCH₂-galabiose-OCH₂CH[CH₂SO₂(CH₂)₇CH₃]CH₂SO₂(CH₂)₁₀COOCH₃
CH₂=CHCH₂O-galabiose-OPh-p-NH₂
CH₂=CHCH₂O-galabiose-O(CH₂)₂SPh-p-NH₂
CH₂=CHCH₂O-galabiose-S(CH₂)₁₀COOCH₃
CH₂=CHCH₂O-galabiose-OCH₃
CH₂=CHCH₂O-galabiose-OCH₂CH₃
CH₂=CHCH₂O-galabiose-OCH₂CH(CH₃)₂
CH₂=CHCH₂O-galabiose-O(CH₂)₂Si(CH₃)₃
CH₂=CHCH₂O-galabiose-O(CH₂)₂S(CH₂)₁₀CO-BSA
CH₂=CHCH₂O-galabiose-O(CH₂)₂S(CH₂)₁₀CO-KLH
CH₂=CHCH₂O-galabiose-O(CH₂)₂S(CH₂)₁₀CO-Latex
CH₂=CHCH₂O-galabiose-O(CH₂)₂S(CH₂)₁₀CO-Glass
CH₂=CHCH₂O-galabiose-O(CH₂)₂S(CH₂)₁₀CO-Silica gel
CH₂=CHCH₂O-galabiose-O(CH₂)₂S(CH₂)₁₀CO-polystyrene
CH₂=CHCH₂O-galabiose-O(CH₂)₂S(CH₂)₁₀CO-sepharose
CH₂=CHCH₂O-galabiose-O(CH₂)₂S(CH₂)₁₀CO-dextran
PhCH₂O-galabiose-O(CH₂)₂S(CH₂)₂COOCH₃
PhCH₂O-galabiose-O(CH₂)₂S(CH₂)₁₀COOCH₃
PhCH₂O-galabiose-O(CH₂)₂S(CH₂)₁₅CH₃
PhCH₂O-galabiose-OCH₂CH[CH₂S(CH₂)₁₅CH₃]₂
PhCH₂O-galabiose-OCH₂CH[CH₂SO₂(CH₂)₁₅CH₃]₂
PhCH₂-galabiose-OCH₂CH[CH₂SO₂(CH₂)₇CH₃]CH₂SO₂(CH₂)₁₀COOCH₃
PhCH₂O-galabiose-OPh-p-NH₂
PhCH₂O-galabiose-O(CH₂)₂SPh-p-NH₂
PhCH₂O-galabiose-S(CH₂)₁₀COOCH₃
PhCH₂O-galabiose-OCH₃
PhCH₂O-galabiose-OCH₂CH₃
PhCH₂O-galabiose-OCH₂CH(CH₃)₂
PhCH₂O-galabiose-O(CH₂)₂Si(CH₃)₃
PhCH₂O-galabiose-O(CH₂)₂S(CH₂)₁₀CO-BSA
PhCH₂O-galabiose-O(CH₂)₂S(CH₂)₁₀CO-KLH
PhCH₂O-galabiose-O(CH₂)₂S(CH₂)₁₀CO-Latex
PhCH₂O-galabiose-O(CH₂)₂S(CH₂)₁₀CO-Glass
PhCH₂O-galabiose-O(CH₂)₂S(CH₂)₁₀CO-Silica gel
PhCH₂O-galabiose-O(CH₂)₂S(CH₂)₁₀CO-polystyrene
PhCH₂O-galabiose-O(CH₂)₂S(CH₂)₁₀CO-sepharose
PhCH₂O-galabiose-O(CH₂)₂S(CH₂)₁₀CO-dextran
(CH₃)₂N-galabiose-O(CH₂)₂S(CH₂)₂COOCH₃
(CH₃)₂N-galabiose-O(CH₂)₂S(CH₂)₁₀COOCH₃
(CH₃)₂N-galabiose-O(CH₂)₂S(CH₂)₁₅CH₃
(CH₃)₂N-galabiose-OCH₂CH[CH₂S(CH₂)₁₅CH₃]₂
(CH₃)₂N-galabiose-OCH₂CH[CH₂SO₂(CH₂)₁₅CH₃]₂
(CH₃)₂N-galabiose-OCH₂CH[CH₂SO₂(CH₂)₇CH₃]CH₂SO₂(CH₂)₁₀COOCH₃
(CH₃)₂N-galabiose-OPh-p-NH₂
(CH₃)₂N-galabiose-O(CH₂)₂SPh-p-NH₂
(CH₃)₂N-galabiose-S(CH₂)₁₀COOCH₃
(CH₃)₂N-galabiose-OCH₃
(CH₃)₂N-galabiose-OCH₂CH₃
(CH₃)₂N-galabiose-OCH₂CH(CH₃)₂
(CH₃)₂N-galabiose-O(CH₂)₂Si(CH₃)₃
(CH₃)₂N-galabiose-O(CH₂)₂S(CH₂)₁₀CO-BSA
(CH₃)₂N-galabiose-O(CH₂)₂S(CH₂)₁₀CO-KLH
(CH₃)₂N-galabiose-O(CH₂)₂S(CH₂)₁₀CO-Latex
(CH₃)₂N-galabiose-O(CH₂)₂S(CH₂)₁₀CO-Glass
(CH₃)₂N-galabiose-O(CH₂)₂S(CH₂)₁₀CO-Silica gel
(CH₃)₂N-galabiose-O(CH₂)₂S(CH₂)₁₀CO-Polystyrene
(CH₃)₂N-galabiose-O(CH₂)₂S(CH₂)₁₀CO-sepharose
(CH₃)₂N-galabiose-O(CH₂)₂S(CH₂)₁₀CO-dextran
CH₃OCH₂O-galabiose-O(CH₂)₂S(CH₂)₂COOCH₃
CH₃OCH₂O-galabiose-O(CH₂)₂S(CH₂)₁₀COOCH₃
CH₃OCH₂O-galabiose-O(CH₂)₂S(CH₂)₁₅CH₃]₂
CH₃OCH₂O-galabiose-OCH₂CH[CH₂S(CH₂)₁₅CH₃]₂
CH₃OCH₂O-galabiose-OCH₂CH[CH₂SO₂(CH₂)₁₅CH₃]₂
CH₃OCH₂O-galabiose-OCH₂CH[CH₂SO₂(CH₂)₇CH₃]CH₂SO₂(CH₂)₁₀COOCH₃
CH₃OCH₂O-galabiose-OPh-p-NH₂
CH₃OCH₂O-galabiose-O(CH₂)₂SPh-p-NH₂
CH₃OCH₂O-galabiose-S(CH₂)₁₀COOCH₃
CH₃OCH₂O-galabiose-OCH₃
CH₃OCH₂O-galabiose-OCH₂CH₃
CH₃OCH₂O-galabiose-OCH₂CH(CH₃)₂
CH₃OCH₂O-galabiose-O(CH₂)₂Si(CH₃)₃
CH₃OCH₂O-galabiose-O(CH₂)₂S(CH₂)₁₀CO-BSA CH$_3$OCH$_2$O-galabiose-O(CH$_2$)$_2$S(CH$_2$)$_{10}$CO-KLH
CH$_3$OCH$_2$O-galabiose-O(CH$_2$)$_2$S(CH$_2$)$_{10}$CO-Latex
CH$_3$OCH$_2$O-galabiose-O(CH$_2$)$_2$S(CH$_2$)$_{10}$CO-Glass
CH$_3$OCH$_2$O-galabiose-O(CH$_2$)$_2$S(CH$_2$)$_{10}$CO-Silica gel
CH$_3$OCH$_2$O-galabiose-O(CH$_2$)$_2$S(CH$_2$)$_{10}$CO-Polystyrene
CH$_3$OCH$_2$O-galabiose-O(CH$_2$)$_2$S(CH$_2$)$_{10}$CO-sepharose
CH$_3$OCH$_2$O-galabiose-O(CH$_2$)$_2$S(CH$_2$)$_{10}$CO-dextran
2-THPO-galabiose-O(CH$_2$)$_2$S(CH$_2$)$_2$COOCH$_3$
2-THPO-galabiose-O(CH$_2$)$_2$S(CH$_2$)$_{10}$COOCH$_3$
2-THPO-galabiose-O(CH$_2$)$_2$S(CH$_2$)$_{15}$CH$_3$
2-THPO-galabiose-OCH$_2$CH[CH$_2$S(CH$_2$)$_{15}$CH$_3$]$_2$
2-THPO-galabiose-OCH$_2$CH[CH$_2$SO$_2$(CH$_2$)$_{15}$CH$_3$]$_2$
2-THPO-galabiose-OCH$_2$CH[CH$_2$SO$_2$(CH$_2$)$_7$CH$_3$]CH$_2$SO$_2$(CH$_2$)$_{10}$COOCH$_3$
2-THPO-galabiose-OPh-p-NH$_2$
2-THPO-galabiose-O(CH$_2$)$_2$SPh-p-NH$_2$
2-THPO-galabiose-S(CH$_2$)$_{10}$COOCH$_3$
2-THPO-galabiose-OCH$_3$
2-THPO-galabiose-OCH$_2$CH$_3$
2-THPO-galabiose-OCH$_2$CH(CH$_3$)$_2$
2-THPO-galabiose-O(CH$_2$)$_2$Si(CH$_3$)$_3$
2-THPO-galabiose-O(CH$_2$)$_2$S(CH$_2$)$_{10}$CO-BSA
2-THPO-galabiose-O(CH$_2$)$_2$S(CH$_2$)$_{10}$CO-KLH
2-THPO-galabiose-O(CH$_2$)$_2$S(CH$_2$)$_{10}$CO-Latex
2-THPO-galabiose-O(CH$_2$)$_2$S(CH$_2$)$_{10}$CO-Glass
2-THPO-galabiose-O(CH$_2$)$_2$S(CH$_2$)$_{10}$CO-Silica gel
2-THPO-galabiose-O(CH$_2$)$_2$S(CH$_2$)$_{10}$CO-polystyrene
2-THPO-galabiose-O(CH$_2$)$_2$S(CH$_2$)$_{10}$CO-sepharose
2-THPO-galabiose-O(CH$_2$)$_2$S(CH$_2$)$_{10}$CO-dextran
PhCH$_2$OCH$_2$O-galabiose-O(CH$_2$)$_2$S(CH$_2$)$_2$COOCH$_3$
PhCH$_2$OCH$_2$O-galabiose-O(CH$_2$)$_2$S(CH$_2$)$_{10}$COOCH$_3$
PhCH$_2$OCH$_2$O-galabiose-O(CH$_2$)$_2$S(CH$_2$)$_{15}$CH$_3$
PhCH$_2$OCH$_2$O-galabiose-OCH$_2$CH[CH$_2$S(CH$_2$)$_{15}$CH$_3$]$_2$
PhCH$_2$OCH$_2$O-galabiose-OCH$_2$CH[CH$_2$SO$_2$(CH$_2$)$_{15}$CH$_3$]$_2$
PhCH$_2$OCH$_2$-galabiose-OCH$_2$CH[CH$_2$SO$_2$(CH$_2$)$_7$CH$_3$]CH$_2$SO$_2$(CH$_2$)$_{10}$COOCH$_3$
PhCH$_2$OCH$_2$O-galabiose-OPh-p-NH$_2$
PhCH$_2$OCH$_2$O-galabiose-O(CH$_2$)$_2$SPh-p-NH$_2$
PhCH$_2$OCH$_2$O-galabiose-S(CH$_2$)$_{10}$COOCH$_3$
PhCH$_2$OCH$_2$O-galabiose-OCH$_3$
PhCH$_2$OCH$_2$O-galabiose-OCH$_2$CH$_3$
PhCH$_2$OCH$_2$O-galabiose-OCH$_2$CH(CH$_3$)$_2$
PhCH$_2$OCH$_2$O-galabiose-O(CH$_2$)$_2$Si(CH$_3$)$_3$
PhCH$_2$OCH$_2$O-galabiose-O(CH$_2$)$_2$S(CH$_2$)$_{10}$CO-BSA
PhCH$_2$OCH$_2$O-galabiose-O(CH$_2$)$_2$S(CH$_2$)$_{10}$CO-KLH
PhCH$_2$OCH$_2$O-galabiose-O(CH$_2$)$_2$S(CH$_2$)$_{10}$CO-Latex
PhCH$_2$OCH$_2$O-galabiose-O(CH$_2$)$_2$S(CH$_2$)$_{10}$CO-Glass
PhCH$_2$OCH$_2$O-galabiose-O(CH$_2$)$_2$S(CH$_2$)$_{10}$CO-Silica gel
PhCH$_2$OCH$_2$O-galabiose-O(CH$_2$)$_2$S(CH$_2$)$_{10}$CO-polystyrene
PhCH$_2$OCH$_2$O-galabiose-O(CH$_2$)$_2$S(CH$_2$)$_{10}$CO-sepharose
PhCH$_2$OCH$_2$O-galabiose-O(CH$_2$)$_2$S(CH$_2$)$_{10}$CO-dextran
[(CH$_3$)$_3$C](CH$_3$)$_2$SiO-galabiose-O(CH$_2$)$_2$S(CH$_2$)$_2$COOCH$_3$
[(CH$_3$)$_3$C](CH$_3$)$_2$SiO-galabiose-O(CH$_2$)$_2$S(CH$_2$)$_{10}$COOCH$_3$
[(CH$_3$)$_3$C](CH$_3$)$_2$SiO-galabiose-O(CH$_2$)$_2$S(CH$_2$)$_{15}$CH$_3$
[(CH$_3$)$_3$C](CH$_3$)$_2$SiO-galabiose-OCH$_2$CH[CH$_2$S(CH$_2$)$_{15}$CH$_3$]$_2$
[(CH$_3$)$_3$C](CH$_3$)$_2$SiO-galabiose-OCH$_2$CH[CH$_2$SO$_2$(CH$_2$)$_{15}$CH$_3$]$_2$
[(CH$_3$)$_3$C](CH$_3$)$_2$SiO-galabiose-OCH$_2$CH[CH$_2$SO$_2$(CH$_2$)$_7$CH$_3$]CH$_2$SO$_2$(CH$_2$)$_{10}$-COOCH$_3$
[(CH$_3$)$_3$C](CH$_3$)$_2$SiO-galabiose-OPh-P-NH$_2$
[(CH$_3$)$_3$C](CH$_3$)$_2$SiO-galabiose-O(CH$_2$)$_2$SPh-p-NH$_2$
[(CH$_3$)$_3$C](CH$_3$)$_2$SiO-galabiose-S(CH$_2$)$_{10}$COOCH$_3$
[(CH$_3$)$_3$C](CH$_3$)$_2$SiO-galabiose-OCH$_3$
[(CH$_3$)$_3$C](CH$_3$)$_2$SiO-galabiose-OCH$_2$CH$_3$
[(CH$_3$)$_3$C](CH$_3$)$_2$SiO-galabiose-OCH$_2$CH(CH$_3$)$_2$
[(CH$_3$)$_3$C](CH$_3$)$_2$SiO-galabiose-O(CH$_2$)$_2$Si(CH$_3$)$_3$
[(CH$_3$)$_3$C](CH$_3$)$_2$SiO-galabiose-O(CH$_2$)$_2$S(CH$_2$)$_{10}$CO-BSA
[(CH$_3$)$_3$C](CH$_3$)$_2$SiO-galabiose-O(CH$_2$)$_2$S(CH$_2$)$_{10}$CO-KLH
[(CH$_3$)$_3$C](CH$_3$)$_2$SiO-galabiose-O(CH$_2$)$_2$S(CH$_2$)$_{10}$CO-Latex
[(CH$_3$)$_3$C](CH$_3$)$_2$SiO-galabiose-O(CH$_2$)$_2$S(CH$_2$)$_{10}$CO-Glass
[(CH$_3$)$_3$C](CH$_3$)$_2$SiO-galabiose-O(CH$_2$)$_2$S(CH$_2$)$_{10}$CO-Silica gel
[(CH$_3$)$_3$C](CH$_3$)$_2$SiO-galabiose-O(CH$_2$)$_2$S(CH$_2$)$_{10}$CO-polystyrene
[(CH$_3$)$_3$C](CH$_3$)$_2$SiO-galabiose-O(CH$_2$)$_2$S(CH$_2$)$_{10}$CO-sepharose
[(CH$_3$)$_3$C](CH$_3$)$_2$SiO-galabiose-O(CH$_2$)$_2$S(CH$_2$)$_{10}$CO-dextran
(CH$_3$)$_3$Si(CH$_2$)$_2$OCH$_2$O-galabiose-O(CH$_2$)$_2$S(CH$_2$)$_2$COOCH$_3$
(CH$_3$)$_3$Si(CH$_2$)$_2$OCH$_2$O-galabiose-O(CH$_2$)$_2$S(CH$_2$)$_{10}$COOCH$_3$
(CH$_3$)$_3$Si(CH$_2$)$_2$OCH$_2$O-galabiose-O(CH$_2$)$_2$S(CH$_2$)$_{15}$CH$_3$
(CH$_3$)$_3$Si(CH$_2$)$_2$OCH$_2$O-galabiose-OCH$_2$CH[CH$_2$S(CH$_2$)$_{15}$CH$_3$]$_2$
(CH$_3$)$_3$Si(CH$_2$)$_2$OCH$_2$O-galabiose-OCH$_2$CH[CH$_2$SO$_2$(CH$_2$)$_{15}$CH$_3$]$_2$
(CH$_3$)$_3$Si(CH$_2$)$_2$OCH$_2$-galabiose-OCH$_2$CH[CH$_2$SO$_2$(CH$_2$)$_7$CH$_3$]CH$_2$SO$_2$(CH$_2$)$_{10}$-COOCH$_3$
(CH$_3$)$_3$Si(CH$_2$)$_2$OCH$_2$O-galabiose-OPh-p-NH$_2$
(CH$_3$)$_3$Si(CH$_2$)$_2$OCH$_2$O-galabiose-O(CH$_2$)$_2$SPh-p-NH$_2$
(CH$_3$)$_3$Si(CH$_2$)$_2$OCH$_2$O-galabiose-OCH$_2$)S(CH$_2$)$_{10}$COOH$_3$
(CH$_3$)$_3$Si(CH$_2$)$_2$OCH$_2$O-galabiose-OCH$_3$
(CH$_3$)$_3$Si(CH$_2$)$_2$OCH$_2$O-galabiose-OCH$_2$CH$_3$
(CH$_3$)$_3$Si(CH$_2$)$_2$OCH$_2$O-galabiose-OCH$_2$CH(CH$_3$)$_2$
(CH$_3$)$_3$Si(CH$_2$)$_2$OCH$_2$O-galabiose-O(CH$_2$)$_2$Si(CH$_3$)$_3$
(CH$_3$)$_3$Si(CH$_2$)$_2$OCH$_2$O-galabiose-O(CH$_2$)$_2$S(CH$_2$)$_{10}$CO-BSA
(CH$_3$)$_3$Si(CH$_2$)$_2$OCH$_2$O-galabiose-O(CH$_2$)$_2$S(CH$_2$)$_{10}$CO-KLH
(CH$_3$)$_3$Si(CH$_2$)$_2$OCH$_2$O-galabiose-O(CH$_2$)$_2$S(CH$_2$)$_{10}$CO-Latex
(CH$_3$)$_3$Si(CH$_2$)$_2$OCH$_2$O-galabiose-O(CH$_2$)$_2$S(CH$_2$)$_{10}$CO-Glass
(CH$_3$)$_3$Si(CH$_2$)$_2$OCH$_2$O-galabiose-O(CH$_2$)$_2$S(CH$_2$)$_{10}$CO-Silica gel
(CH$_3$)$_3$Si(CH$_2$)$_2$OCH$_2$O-galabiose-O(CH$_2$)$_2$S(CH$_2$)$_{10}$CO-polystyrene
(CH$_3$)$_3$Si(CH$_2$)$_2$OCH$_2$O-galabiose-O(CH$_2$)$_2$S(CH$_2$)$_{10}$CO-sepharose
(CH$_3$)$_3$Si(CH$_2$)$_2$OCH$_2$O-galabiose-O(CH$_2$)$_2$S(CH$_2$)$_{10}$CO-dextran Note on abbreviations:

GalN=D-galactosamine; Gal=D-galactose; Ac=acetyl; Phth=phthaloyl; Ph=phenyl; 2-THP=tetrahydropyranyl; p=para position; BSA bovine serum albumin; KLH=keyhole limpet haemocyanin; Latex, glass, polystyrene, sepharose and dextran=particles, films and layers.

Other interesting aglycon moieties —XR$_1$ are —S—CH$_2$CH$_3$, —O—CH$_2$CH[CH$_2$SO$_2$(CH$_2$)$_3$CH$_3$]$_2$, —S—CH$_2$CH[CH$_2$SO$_2$(CH$_2$)$_3$CH$_3$]$_2$, and —CH$_2$—CH$_2$CH[CH$_2$SO$_2$(CH$_2$)$_3$CH$_3$]$_2$, and each of these groups may be combined with each of the R$_2$Y-galabiose moieties listed in the compounds above, namely GalNAcβO-galabiose-, GalNPhthβO-galabiose-, GalαO-galabiose-, CH$_3$O-galabiose-, CH$_3$CH$_2$O-galabiose-, (CH$_3$)$_2$CHO-galabiose-, CH$_2$=CHCH$_2$O-galabiose-, PhCH$_2$O-galabiose-, (CH$_3$)$_2$N-galabiose-, CH$_3$OCH$_2$O-galabiose-, 2-THPO-galabiose-, PhCH$_2$OCH$_2$O-galabiose-, [(CH$_3$)$_3$C](CH$_3$)$_2$SiO-galabiose-, and (CH$_3$)$_3$Si(CH$_2$)$_2$O-galabiose-.

The compounds of the invention can be prepared according to several general methods which generally require protection of all or most of those hydroxyl groups that are not required to undergo chemical modification.

Since the chemical modification of the galabiose structure is only carried out in on the one hand the anomeric position (or 1-position) and on the other hand in the 3-position in the non-reducing galactose unit (or the 3'-position), the compounds of the invention can be prepared either by first carrying out the desired modification in galactose followed by the creation of a 1–4 glycosidic bond to another unmodified galactose unit that may already be bound to the desired group-XR$_1$ in the 1-position or, if not, the synthesis is then followed by glycosidation to the —XR$_1$ group in the 1-position of the unmodified galactose unit.

When modifying a single galactose unit, in a first strategy a), it is preferred to start out with a unit that is β-glycosidically bound to an aglycon group such as methoxy in order to provide regioselectivity and prevent the 1-hydroxy group from taking part in any reactions.

The first step is to protect the 4- and 6-hydroxy groups, preferably by means of acetal formation with benzaldehyde or a corresponding acetal thereof such as dimethoxytoluene. The latter reaction is preferably carried out in a polar, aprotic solvent such acetonitrile and with an acid catalyst such as p-toluene sulfonic acid. As a result of the protection, the two remaining unprotected hydroxy groups are those in the 2- and 3-positions. For the preparation of compounds of the formula I in which y is oxygen, the 4,6-protected galactose derivative is then reacted with a compound R$_2$—L (where L is a leaving group) catalyzed by means of a base. The reaction may be carried out in an aprotic, polar or apolar solvent such as an ether (e.g. tetrahydrofuran, diethylether etc), an aromatic hydrocarbon (e.g. toluene), a halogenated hydrocarbon (e.g. methylene chloride, chloroform etc.), dimethyl formamide, dimethyl sulphoxide or pyridine. The reaction may be carried out at temperatures between −80° C. and +150° C., preferably between −40° C. and 100° C. The reaction favours substitution in the 3-position over substitution in the 2-position due to the β-oriented aglycon, but any unwanted 2-substituted product may easily be removed by e.g. column chromatography.

Thereafter, the 4,6-protecting acetal group is removed, preferably by treatment with I$_2$ in methanol at reflux temperature. This treatment selectively removes the benzylydine acetal group without affecting other protecting groups. The resulting 3-modified and 2,4,6-unprotected galactose derivative is then protected in the 2-, 4- and 6-positions by treatment with benzyl bromide under basic conditions in a manner known per se prior to treatment with aqueous acid to remove the anomeric protecting group prior to glycoside synthesis in a manner known per se.

In another approach b), the single galactose unit is modified in the 3-position when all the other hydroxy groups are selectively protected. Such a selectively 3-unprotected galactose derivative as a starting compound can be obtained in a 4-step synthesis in which 1-glycosidated but otherwise unprotected galactose is reacted with two equivalents of 2,2-dimethoxy propane in an acid medium to form a compound in which the 3- and 4-hydroxy groups are protected in a cyclic acetal, and the 6-hydroxy group is protected with a 2 methoxy-propane-2-yl group, leaving only the 2-hydroxy group unprotected. Reaction with benzyl bromide in a basic medium followed by treatment with aqueous acid gives a galactose derivative which is benzylated in the 2-position and glycosidated in the 1-position but otherwise unprotected. Reaction thereof with benzaldehyde as described above gives a derivative which is protected in the 2-, 4- and 6-positions but unprotected in the 3-position. Thereafter, the 3-position is modified with R$_2$—L as above followed by removal of the benzylacetal group as above and benzylation and deglycosidation as above prior to glycoside synthesis with another galactose unit.

Yet another approach c) exploits the fact that the reaction between R$_2$—L and a galactose derivative that is unprotected in the 3- and 4-positions is also selective with respect to the 3-position over the 4-position. For this purpose, 1-glycosidated galactose is reacted with one equivalent of 2,2-dimethoxy propane or acetone giving a galactose derivative that is protected with a cyclic group in the 3- and 4-positions but unprotected in the 2- and 6-positions. Benzylation in the normal manner of the 2- and 6- hydroxy groups followed by removal of the cyclic acetal group by treatment with aqueous acid gives a galactose derivative in which the 2- and 6- hydroxy groups are benzylated but the 3- and 4- hydroxy groups are unprotected. Reaction of this compound with R$_2$—L in a basic environment as above gives predominantly the 3-modified compound where Y is O, and any 4-modified byproduct can easily be removed by e.g. column chromatography. Benzylation of the remaining unprotected 4-hydroxy group followed by removal of the aglycone in the 1-position by treatment with aqueous acid paves the way for glycoside synthesis with another galactose unit. The benzylation with benzyl bromide may be carried out in a protic solvent such as toluene, dimethyl formamide or methylene chloride, preferably at reflux temperature. The bases used in the reaction (and in the same type of reactions above) are a preferably strong bases such as potassium hydroxide or sodium hydride.

Following glycoside synthesis with another galactose unit, the protecting benzyl groups in the 2-, 4-, and 6-positions of the galabiose products may be removed by catalytic hydrogenation in e.g. acetic acid or ethanol/perchloric acid, preferably over a catalyst such as palladium on carbon.

If it is desired to work upon an already established galabioside, this may be carried out by starting from a 1–4-galabioside which is benzoylated in the 2-, 3- and 6-positions in the reducing galactose unit and benzylated in the 2-, 3-, 4- and 6-positions in the nonreducing galactose unit (the 2'-, 3'-, 4'- and 6'-positions), this compound being known. First of all, the benzyl protecting groups in the non-reducing galactose unit are removed by hydrogenolysis over Pd/C in a known manner giving the starting compound, in the following termed GG. Thereafter, compounds GG is, as in strategy a) above, reacted with two equivalents of 2,2-dimethoxypropane or acetone followed by treatment with sodium methoxide in methanol at 20° C. (followed by neutralization) to remove the benzoyl groups in the reducing galactose unit. Thereafter, one proceeds as in strategy b) above, that is reaction with benzyl bromide in base, hydrolysis in aqueous acetic acid, and reaction with benzaldehyde to give the 3-unprotected galabiose derivative which is then reacted with R$_2$—L as above followed by removal of the protecting groups as above. If the aglycon in the anomeric position is not the one desired, the aglycon can be removed in the usual manner and the resulting 3-modified galabiose subjected to glycoside synthesis in the usual manner.

In another approach, one exploits the properties of strategy c) above in which derivation in the 3-position predominates over derivation in the 4-position. In this method, the starting compound GG is treated with acetone in an acid medium causing the non-reducing galactose unit to be protected in the 3- and 4-positions. Treatment with sodium methoxide as above to remove the benzoyl groups in the reducing galactose unit followed by treatment with benzylbromide as described above gives a galabiose derivative which is protected as an acetal in the 3'- and 4'-positions but benzylated everywhere else, and this compound is then deprotected in the 3'- and 4'-positions by means of aqueous acid and treated with $R_2$—L as above whereby modification of the 3-hydroxy group predominates over modification in the 4'-position. Finally, the benzyl protecting groups are removed by hydrogenolysis as above.

Compounds in which Z is —O—, —S—, and —$SO_2$—, and in which X is —O—, —S—, —$SO_2$— and —$NR_3$—, can be prepared according to methods that are well described in the literature. Compounds in which Z and/or X is —$CH_2$—, namely the so-called C-disaccharides and C-glycosides, respectively, can be prepared according to the general principles described by S. A. Babirad, Y. Wang & Y. Kishi, *J. Org. Chem.* (1987), 52, 1370–1372, and R. Bihousky, C. Selick & I. Giusti, *J. Org. Chem.* (1988), 53, 4026–4031.

Due to their ability of being bound strongly to adhesins in bacteria, compounds of the invention may be used for diagnostic purposes as diagnostic devices or kits. In one embodiment, a diagnostic device could consist of a dip-stick or a microtiter plate having compounds of the formula I immobilized on the surface of the stick or in the wells of the microtiter plate, either covalently or by for example hydrophobic interaction. A typical manner for using such diagnostic devices would be to bring the dip-stick or microtiter plate into contact with a bacteria-containing sample such as a urine sample to allow the bacteria to adhere to the compounds immobilized on the surface of the device. This operation would then be followed by a rinsing procedure to remove all traces of the sample from the device except the bacteria adhered on the surface. Thereafter, the adhered bacteria would be treated with a solution containing antibodies (e.g. monoclonal antibodies) raised against the bacteria in question. The antibodies would preferably be labelled in some way, either radioactively or enzymatically In case of radioactive labelling, the dipstick or microtiter plate would then after rinsing be tested for radioactivity, and in the case of presence of radioactivity on the surface of the device, this would indicate the presence of the bacteria. In case of enzymatic labelling, the antibody reaction process would be followed by a detection process in which a reagent is brought into contact with the device, and if bound labelled antibodies are present, this would give rise to e.g. a colour reaction indicating the presence of bacteria.

In another embodiment, the presence of bacteria in a sample could be tested by means of an agglutination reaction where e.g. small latex particles coated with a compound of the invention are brought into contact with the sample to be tested for bacteria. If bacteria are present in the sample, the bacteria will bind themselves to the surfaces of several latex particles and thereby give rise to the formation of a precipitate which could then be detected either visually or by optical means.

A diagnostic kit could for instance comprise the above mentioned diagnostic dip-sticks or microtiter plates together with the necessary antibody solutions, latex suspensions, colour reagent, test solutions etc.

Other possible embodiments of such diagnostic tools would be test cards like the type used for blood tests in which the necessary components are comprised in a gel layer on the card.

With respect to treatment or prophylaxis against bacterial infections, one important use aspect is in connection with epithelial cells and the port-of-entry of various infections. Examples of such port-of-entries are the mucous membranes of the eye, nose, oral cavity, throat, respiratory tract, gastrointestinal tract, urinary tract and reproductive organs. Treatment or prophylaxis may be obtained by direct application to the mucous membranes of the compounds of the formula I in a pharmaceutically acceptable form such as a suspension, an aerosol, an ointment, a gel or a solution. On the mucous membranes, the active compounds will bind to bacteria, thereby reducing the infecting ability of the organism. The compound of the formula I may, however, also conceivably be used as systemic agents for intravenous, intramuscular, tetraperitoneal or subcutaneous injection. The composition for this use may be in the form of a solution, an emulsion or a suspension of either compounds in solid form or the compounds incorporated on various of the carriers described above. The compounds of the formula I may furthermore be administered in the form of nasal or oral sprays.

Other uses of the compound of the formula I include flushing of the urinary tract, intestines etc.

In view of the above, the present invention therefore also relates to pharmaceutical or diagnostic compositions comprising one or more compounds of the formula I, optionally in combination with a pharmaceutically acceptable carrier or excipient.

The pharmaceutical composition may be in the form of tablets, capsules, lozenges, syrups, injectable solutions, injectable emulsions, implants or suppositories. The excipient may be any of the excipients commonly used within the art. For solid compositions, conventional non-toxic solid excipients may be used including e.g. pharmaceutical grades of mannitol, lactose, starch, magnesium stearate, sodium saccharin, talc, cellulose, glucose, saccharose, magnesium carbonate or the like. Liquid pharmaceutically administerable compositions may e.g. be prepared by dissolving, dispersing etc. the active compound and an optional, pharmaceutical adjuvant in an excipient such as water, saline, aqueous dextrose, glycerol, ethanol etc. in order to form a solution or suspension. If desired, the pharmaceutical composition to be administered may also contain minor amounts of non-toxic additives such as wetting or emulsifying agents, pH-buffers etc., for example sodium acetate, sorbitan monolaurate, triethanolamine etc. The active compound may also be formulated as suppositories using e.g. polyalkylene glycols such as propylene glycol as an excipient. The actual preparation of such dosage forms are well known or will be evident to persons skilled in the art, cf. e.g. *Remington's Pharmaceutical Sciences*, Mack Publishing Company, Easton, Pa., 15th Edition, 1975.

For intravenous injection, the compounds (optionally bound to a carrier) is dissolved in a aqueous medium buffered to the desired pH and treated in order to control isotonicity.

Since the compounds of the formula I are useful in connection with the mucous membranes, the compounds may also be administered in the form of an aerosol.

When administered as an aerosol, the active compound is preferably given in a finely divided form together with a surfactant and a propellant.

The dosages at which the compounds of the formula I are to be administered may vary widely depending on the intended use whether for prophylaxis including disinfection or therapy, the type of infection to be combated, the age and condition of the patient etc. but is expected to be at milligram level. However, contrary to what is the case with most pharmaceuticals now in use, the dosage level may not be so essential since the toxic effects of the compounds of formula I are expected to be negligeable since the compounds closely resemble the natural receptors which are present in large amounts in the human or animal system.

Another possible use is disinfection means such as fluids (for cleaning e.g. surgical wounds) or paper tissues incorporating specific receptors towards certain bacteria such as bacteria transmitting various infectious diseases.

The invention is further illustrated by the following non-limiting examples.

EXAMPLE 1

Methyl 4,6-O-benzylidene-3-(A) and 2-O-methyl-β-D-galactopyranoside (B).

Aqueous sodium hydroxide (1.25M; 20 ml) was added to C (1.00 g, 3.55 mmol), tetrabutylammonium hydrogensulfate (0.24 g, 0.70 mmol), and methyl iodide (0.64 ml, 10.3 mmol) in dichloromethane (60 ml). The mixture was boiled under reflux with vigorous stirring for 48 h and three portions of methyl iodide (each 0.64 ml, 10.3 mmol) were added after 6, 24, and 32 h, respectively. The aqueous phase was extracted with dichloromethane (40 ml), and the combined organic extracts were dried and concentrated. Column chromatography (ethyl acetate) of the residue gave A (340 mg, 32%) and B (227 mg, 22%). Compound A had mp 216°–217° C., $[\alpha]_D^{25}=+25°$ (C=0.79, chloroform).

$^1$H-NMR data (CDCl$_3$, plus 1 drop of D$_2$O): δ8 5.56 (s, 1H, PhCH), 4.37 (dd, 1H, J 12.3 and 1.3 Hz, H-6), 4.33 (dd, 1H, J 3.5 and 1.1 Hz, H-4), 4.27 (d, 1H, J 7.8 Hz, H-1), 4.11 (dd, 1H, J 12.3 and 1.8 Hz, H-6), 3.4 (dd, 1H, J 9.8 and 7.8 Hz, H-2, shifted to δ5.31 on acetylation), 3.59 (s, 3H, MeO), 3.53 (s, 3H, MeO), 3.45 (q, 1H, J 1.5 Hz, H-5), 3.34 (dd, 1H, J 9.8 and 3.2 Hz, H-3).

Anal. Calc. for C$_{15}$H$_{20}$O$_6$: C, 60.8; H, 6.8. Found: C, 60.7; H, 6.8.

Compound B had mp 169°–171° C., $[\alpha]_D^{25}=-29°$ (c=0.69, chloroform), $^1$H-NMR data (CDCl$_3$, plus 1 drop of D$_2$O): δ5.56 (s, 1H, PhCH), 4.35 (dd, 1H, J 12.4 and 1.6 Hz, H-6), 4.23 (d, 1H, J 7.6 Hz, H-1); 4.21 (dd, 1H, J 4.1 and 1.3 Hz, H-4), 4.08 (dd, 1H, J 12.4 and 2.1 Hz, H-6), 3.66 (dd, 1H, J 9.6 and 4.1 Hz, H-3, shifted to δ4.82 on acetylation), 3.63 (s, 3H, MeO), 3.58 (s, 3H, MeO), 3.45 (q, 1H, J 1.6 Hz, H-5), 3.32 (dd, 1H, J 9.6 and 7.6 Hz, H-2).

Anal. Calc. for C$_{15}$H$_{20}$O$_6$: C, 60.8; H, 6.8. Found: C, 60.4; H, 6.7.

Methyl 2,4,6-tri-O-benzyl-3-O-methyl-β-D-galactopyranoside (D)

Pd/C (10%, 150 mg) was added to a solution of A (245 mg, 0.83 mmol) in acetic acid (10 ml). The mixture was hydrogenated for 3 h at atmospheric pressure, then filtered through Celite, and concentrated. Freeze-drying of a solution of the syrupy residue in water (5 ml) gave amorphous methyl 3-O-methyl-β-D-galactopyranoside that was dissolved in dry N,N-dimethylformamide (5 ml). Sodium hydride (50% in oil, 180 mg, 3.74 mmol) was added to the solution at 0° C., followed by benzyl bromide (445 μl, 3.74 mmol) after 10 min and the mixture was stirred at 60° C. for 30 min. Methanol (305 μl) was added and after 30 min. the mixture was diluted with ether (40 ml), washed with water (4×10 ml), dried, and concentrated. Column chromatography (ethyl acetate-heptane, 1:5) of the residue gave D (340 mg, 86%), m.p. 56°–58° C., $[\alpha]_D^{25}=16°$ (c=0.78, chloroform).

$^1$H-NMR data (CDCl$_3$): δ4.25 (d, 1H, J 7.7 Hz, H-1), 3.91 (bd, 1H, J 2.9 Hz, H-4), 3.70 (dd, 1H, J 9.7 and 7.7 Hz, H-2), 3.53 (s, 3H, MeO), 3.50 (s, 3H, MeO), 3.26 (dd, 1H, J 9.7 and 2.9 Hz, H-3).

Anal. Calc. for C$_{29}$H$_{34}$O$_6$: C, 72.8; H, 7.2. Found: C, 72.8; H, 7.2.

2,4,6-Tri-O-benzyl-3-O-methyl-D-galactopyranose (E)

A solution of D (3.56 g, 7.45 mmol) in acetic acid-M aqueous hydrogen chloride (7:2, 90 ml) was stirred for 1 h at 100° C., then diluted with dichloromethane (250 ml), washed with saturated aqueous sodium hydrogencarbonate (3×100 ml), dried and concentrated. Column chromatography (ethyl acetate-heptane, 1:3) of the residue gave 6 (2.39 g, 69%), mp 56°–25 $[\alpha]_D^{25}=+5°$ (c=0.55, chloroform).

Anal. Calc. for C$_{28}$H$_{32}$O$_6$: C, 72.4; H, 6.9. Found: C, 71.9; H, 7.0.

Methyl 2,3,6-tri-O-benzoyl-4-O-(2,4,6-tri-O-benzoyl-3-O-methyl-α-D-galactopyranosyl)-β-D-galactopyranoside (F)

A mixture of methyl 2,3,6-tri-O-benzoyl-β-D-galactopyranoside (AA) (954 mg, 1.89 mmol) (cf. Garegg, P. J. and S. Oscarsson, *Carbohydr. Res.*, 137 (1985), 270–275), silver trifluoromethanesulfonate (727 mg, 2.83 mmol), and molecular sieves (4 Å, 1.2 g) was dried overnight at 0.1 torr. Dry toluene (27 ml) and 2,4,6-trimethylpyridine (374 μl, 2.83 mmol) were added with stirring and the mixture was cooled to −40° C. under nitrogen. A solution of freshly prepared 2,4,6-tri-O-benzyl-3-O-methyl-D-galactopyranosyl chloride (ca. 1.5 mmol) in dry toluene (4.5 ml) was added with protection from light and the mixture was allowed to attain room temperature, then filtered through Celite, and diluted with dichloromethane (100 ml) 11. The solution was washed with M aqueous hydrogen chloride (20 ml) and saturated aqueous sodium hydrogencarbonate (20 ml), dried and concentrated. Column chromatography (ethyl acetate-heptane, 1:5) of the residue gave E (640 mg, 45%) as a syrup and recovered 20 (496 mg). Compound E had $[\alpha]_D^{25}=+42°$ (c=0.43, chloroform).

$^1$H-NMR data (CDCl$_3$): δ5.76 (dd, 1H, J 10.4 and 7.7 Hz, H-2), 5.20 (dd, 1H, J 10.4 and 2.8 Hz, H-3), 4.90 (d, 1H, J 3.6 Hz, H-1'), 4.62 (d, 1H, J 7.7 Hz, H-1), 4.39 (bd, 1H, J 2.8 Hz, H-4), 4.32 (dd, 1H, J 9.8 and 4.7 Hz, H6 or H6'), 4.10 (bs, 1H, H-4'), 4.05 (bt, 1H, J 6.8 Hz, H-5 or H-5'), 3.98 (dd, AB-type, 1H, J 10.3 and 3.6 Hz, H-2'), 3.90 (dd, AB-type, 1H, J 10.3 and 2.6 Hz, H-3'), 3.55 (s, 3H, MeO), 3.54 (s, 3H, MeO), 3.36 (dd, 1H, J 9.5 and 8.5 Hz, H6 or H6'), 2.84 (dd, 1H, J 8.3 and 4.9 Hz, H-5 or H-5').

Anal. Calc. for C$_{56}$H$_{56}$O$_{14}$: C, 70.6; H, 5.9. Found: C, 70.4; H, 6.1.

Methyl 4-O-(3-O-methyl-α-D-galactopyranosyl)-β-D-galactopyranoside (11)

A solution of F (628 mg, 0,660 mmol) in dichloromethane-methanolic 0.1M sodium methoxide (1:1, 16 ml) was stirred for 6 h at room temperature, then neutralized (Duolite (H$^+$) resin), and concentrated. Pd/C (10%, 400 mg) was added to a solution of the crude methyl 4-O-(2,4,6-tri-O-benzyl-3-O-methyl-α-D-galactopyranosyl)-β-D-galactopyranoside in acetic acid (10 ml). The mixture was hydrogenated for 5 h at atmospheric pressure, then filtered through Celite, and concentrated. Column chromatography (ethanol-dichloromethane, 1:3) of the residue gave, after freeze-drying, amorphous 11 (210 mg, 86%), $[\alpha]_D^{25}=+121°$ (c=1.4, water).

$^1$H-NMR data (D$_2$O): δ4.93 (d, 1H, J 3.6 Hz, H-1'), 4.36 (d, 1H, J 7.9 Hz, H-1), 4.30 (t, 1H, J 6.4 Hz, H-5'), 4.28 (bd, 1H, J 3.2 Hz, H-4'), 4.01 (bd, 1H, J 2.9 Hz, H-4), 3.85 (dd, 1H, J 10.0 and 3.6 Hz, H-2'), 3.71 (dd, 1H, J 10.4 and 2.9 Hz, H-3), 3.57 (dd, 1H, J 10.0 and 3.2 Hz, H-3'), 3.56 (s, 3H, MeO-1), 3.51 (dd, 1H, J 10.4 and 7.9 Hz, H-2), 3.42 (s, 3H, MeO–3').

17

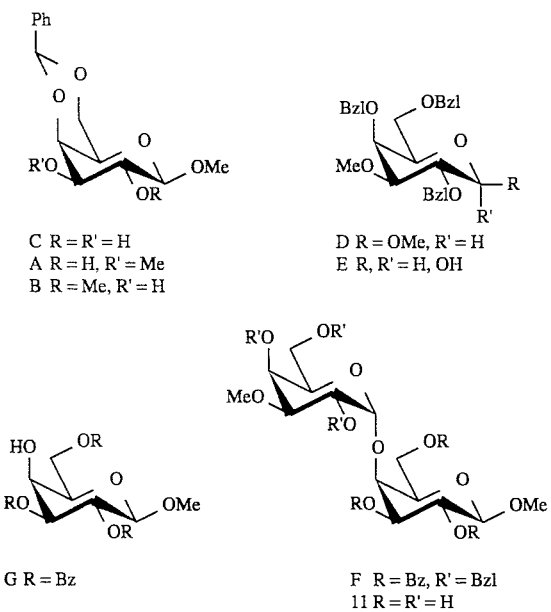

C R = R' = H
A R = H, R' = Me
B R = Me, R' = H

D R = OMe, R' = H
E R, R' = H, OH

G R = Bz

F R = Bz, R' = Bzl
11 R = R' = H

EXAMPLE 2

3-Butylthio-2-butylthiomethylpropyl 2,3,6-tri-O-acetyl-4-O-(2,3,4,6-tetra-O-acetyl-α-D-galactopyranosyl)-β-D-galactopyranoside (G)

A mixture of 3-bromo-2-bromomethylpropyl 2,3,6-tri-O-acetyl-4-O-(2,3,4,6-tetra-O-acetyl-α-D-galactopyranosyl)-β-D-galactopyranoside (220 mg, 0.259 mmol; Carbohydr. Res., 161 (1987) 225–233), butylmercaptan (70 mg, 83 µl, 0.78 mmol), cesium carbonate (202 mg, 0.621 mmol), and dry N,N-dimethylformamide (2.5 ml) was stirred overnight and then worked up essentially as described for similar compounds in the reference given above. Column chromatography ($SiO_2$, ethyl acetate-heptane 3:2) gave 23 (141 mg, 63%), $[\alpha]_D^{25}$=72° (c=1, $CHCl_3$).

$^1$H-NMR data ($CDCl_3$): δ5.58 (dd, 1H, d 1.2 and 3.3 Hz, H-4'), 5.38 (dd, 1H, J 3.3 and 11.0 Hz, H-2'), 5.20 (dd, 1H, J 3.6 and 11.1 Hz, H-3'), 5.16 (dd, 1H, J 7.7 and 10.9 Hz), H-2), 4.99 (d, 1H, J 3.7 Hz, H-1'), 4.80 (dd, 1H, J 2.8 and 10.8 Hz, H-3), 4.45 (d, 1H, J 7.8 Hz, H-1), 2.55–2.70, 2.45–2.55 (m, 4H each, $CH_2S$), 1.50–1.63, 1.34–1.47 (m, 4H each, $SCH_2CH_2CH_2$), 0.91 (t, 6H, J 7.3 Hz, $CH_3$).

Anal. Calc. for $C_{38}H_{60}O_{18}S_2$: C, 52.5; H, 7.0. Found: C, 52.6; H, 6.9.

3-Butylsulfonyl-2-butylsulfonylmethylpropyl 2,3,6-tri-O-acetyl-4-O-(2,3,4,6-tetra-O-acetyl-α-D-galactopyranosyl)-β-D-galactopyranoside (H)

Compound G (368 mg, 0.424 mmol) was dissolved in dry ethyl acetate (15 ml), m-chloroperbenzoic acid (488 mg, 2.12 mmol) was added and the mixture was stirred for 1 h. The mixture was filtered through alumina (8.5 g, 5×4 ml $CH_2Cl_2$). The solvent was removed and the residue was chromatographed ($SiO_2$, ethyl acetate-heptane 3:2) to give H (364 mg, 92%), $[\alpha]_D^{25}$=61° (c=1, $CDCl_3$).

$^1$H-NMR data ($CDCl_3$): δ5.57 (dd, 1H, J 1.1 and 3.3 Hz, H-4'), 5.39 (dd, 1H, J 3.4 and 11.0 Hz, H-2'), 5.21 (dd, 1H, J 3.6 and 11.0 Hz, H-3'), 5.15 (dd, 1H, J 7.8 and 10.9 Hz, H-2), 4.97 (d, 1H, J 3.4 Hz, H-1'), 4.79 (dd, 1H, J 2.7, 11.0 Hz, H-3), 4.51 (d, 1H, J 7.8 Hz, H-1), 3.30–3.45, 3.14–3.25 (m, 2H each, $CH_2SO_2$), 3.00–3.09 (m, 4 H, $CH_2SO_2$), 1.78–1.90, 1.42–1.55 (m, 4H each, $SO_2CH_2CH_2CH_2$), 0.973 (t, 3H, J 7.4 Hz, $CH_3$), 0.969 (t, 3H, J 7.4 Hz, $CH_3$).

18

Anal. Calc. for $C_{38}H_{60}O_{22}S_2$: C, 48.9; H, 6.5. Found: C, 48.4; H, 6.4.

3-Butylsulfonyl-2-butylsulfonylmethylpropyl 4-O-α-D-galactopyranosyl-β-D-galactopyranoside (27)

Compound H (32 mg, 0.034 mmol) was deacetylated and purified essentially as described for similar compounds in Carbohydr. Res. 161 (1987) 225–233 to give 27 (215 mg, 94%), $[\alpha]_D^{25}$=+58° (c=1.3, $Me_2SO$-$d_6$).

$^1$H-NMR data ($D_2O$): δ4.82 (d, 1H, J 3.8 Hz, H-1'), 4.13 (d, 1H, J 7.2 Hz, H-1), 0.90 (t, 6H, J 7.3 Hz, $CH_2CH_3$).

$^{13}$C-NMR data ($Me_2SO$-$d_6$): δ104.1, 100.6, 77.1, 74.5, 72.7, 71.1, 70.8, 69.6, 69.2, 68.8, 68.7, 60.4, 59.1, 52.23, 52.19, 51.6, 51.4, 29.0, 23.32, 23.26, 20.9 (2C), 13.4 (2C).

EXAMPLE 3

Ethyl 1-thio-2,3,6-tri-O-acetyl-4-O-(2,3,4,6-tetra-O-acetyl-α-D-galactopyranosyl)-β-D-galactopyranoside (I)

1,2,3,6-Tetra-O-acetyl-4-O-(2,3,4,6-tetra-O-acetyl-α-D-galactopyranosyl)-β-D-galactopyranose (244 mg, 0.360 mmol; Carbohydr. Res. 113 (1983), 219–224) and ethanethiol (40.0 µl, 33.6 mg, 0.541 mmol) were dissolved in dry dichloromethane (1.4 ml) and borontrifluoride etherate (220.3 µl, 255 mg, 1.77 mmol) was added at −60° C. The mixture was kept at −14° C. overnight, dichloromethane (2.7 ml) was added, and the mixture was washed with water (6 ml), saturated sodium hydrogencarbonate (6 ml) and water (6 ml), then dried ($Na_2SO_4$) and concentrated. Column chromatography ($SiO_2$, ethyl acetate-heptane, 1:1) of the residue gave I (54 mg, 22%, $R_f$ 0.19) as a syrup, ethyl 1-thio-2,3,6 -tri-O-acetyl-4-O-(2,3,4,6-tetra-O-acetyl-α-D-galactopyranosyl)-α -D-galactopyranoside [Iα, 14 mg, 6%, $R_f$ 0.24; $[\alpha]_D^{25}$=+137° (c=1, $CHCl_3$)], and unreacted starting material (110 mg, 45%, $R_f$ 0.13). I had $[\alpha]_D^{25}$=+69° (c=0.7, $CHCl_3$).

$^1$H-NMR data ($CDCl_3$): δ5.57 (dd, 1H, J 3.2 and 1.3 Hz, H-4'), 5.37 (dd, 1H, J 11.1 and 3.2 Hz, H-3'), 5.30 (dd, 1H, J 10.2 and 9.9 Hz, H-2), 5.21 (dd, 1H, J 11.1 and 3.6 Hz, H-2'), 5.02 (d, 1H, J 3.6 Hz, H-1'), 4.89 (dd, 1H, J 10.2 and 2.7 Hz, H-3), 4.46–4,53 (m, 2H, H-4 and H-5 or -5'), 4.48 (d, 1H, J 9.9 Hz, H-1), 4.07–4.19 (m, 4H, H-6,6'), 3.83 (t, 1H, J 6.7 Hz, H-5 or 5'), 2.64–2.85 (m, 2H, $SCH_2$), 1.30 (t, 3H, J 7.5 Hz, $CH_2CH_3$).

Anal. Calc. for $C_{28}H_{40}O_{17}S$: C, 49.4; H, 5.9. Found: C, 49.8; H, 6.0.

Ethyl 1-thio-4-O-(α-D-galactopyranosyl)-β-D-galactopyranoside (28)

Compound I (80.7 mg, 0.118 mmol) was dissolved in methanol-dichloromethane (9:2, 11 ml) and methanolic sodium methoxide (0.5 ml, 0.2M) was added. The mixture was left at room temperature for 2 h, then neutralized (Duolite-H$^+$ resin), filtered and concentrated. Column chromatography ($SiO_2$, CMH: 65:35:6) of the residue and freeze-drying of the product gave 28 (35 mg, 83%) as an amorphous solid, $[\alpha]_D^{25}$=+67° (c=1, $D_2O$).

$^1$H-NMR data ($D_2O$): δ4.93 (d, 1H, J 3.7 Hz, H-1'), 4.57 (d, 1H, J 9.7 Hz, H-1), 4.33 (t, 1H, J 6.4 Hz, H-5'), 4.05 (d, 1H, J 2.9 Hz, H-4'), 4.01 (d, 1H, J 3.1 Hz, H-4), 3.74 (dd, 1H, J 9.8 and 3.1 Hz, H-3), 3.54 (t, 1H, J 9.8 Hz, H-2), 2.65–2.84 (m, 2H, $SCH_2$), 1.26 (t, 3H, J 7.4 Hz, $CH_2CH_3$).

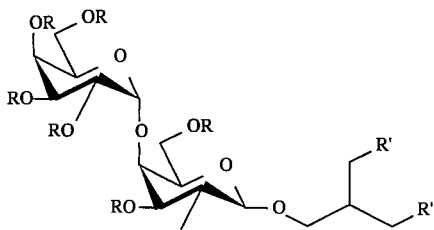

G  R = Ac, R' = S(CH$_2$)$_3$CH$_3$
H  R = Ac, R' = SO$_2$(CH$_2$)$_3$CH$_3$
27 R = H, R' = SO$_2$(CH$_2$)$_3$CH$_3$

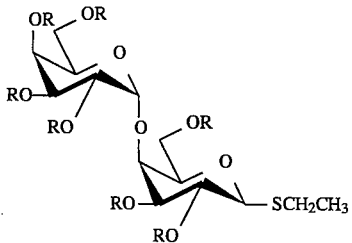

I   R = Ac
28  R = H

EXAMPLE 4

2-(Trimethylsilyl)ethyl-2,3,6-tri-O-benzoyl-β-D-galactopyranoside (K)

Benzoyl chloride (193 μl) was added dropwise to a solution of I (116 mg, 0.414 mmol) in dry acetone (0.8 ml) and dry pyridine (132 μl) at −78° C. After 8 h, methanol (0.1 ml) was added and the temperature was allowed to rise overnight. The solution was diluted with dichloromethane (5 ml), washed with water (2×5 ml), dried (Na$_2$SO$_4$), filtered and concentrated. Column chromatography (SiO$_2$, toluene-ethyl acetate, 50:1→10:1 gradient) of the residue gave K (129 mg, 53%), [α]$_D^{25}$=+49° (c=1.02, chloroform).

$^1$H-NMR data (CDCl$_3$): δ5.75 (dd, 1H, J 7.9 and 10.3 Hz, H-2), 5.34 (dd, 1H, J 3.2 and 10.3 Hz, H-3), 4.75 (d, 1H, J 7.9 Hz, H-1), 4.70 (dd, 1H, J 6.6 and 11.4 Hz, H-6), 4.62 (dd, 1H, J 6.5 and 11.4 Hz, H-6), 4,35 (brd, 1H, H-4), 4.07 (brt, 1H, H-5), 4,03 (m, 1H, OCH$_2$CH$_2$), 3.62 (m, 1H, OCH$_2$CH$_2$), 1.01–0.81 (m, 2H, CH$_2$CH$_2$Si); −0.09 (s, 9H, —Si(CH$_3$)$_3$).

Anal. Calc. for C$_{32}$H$_{36}$O$_9$Si: C, 64.8; H, 6.1. Found: C, 64.5; H, 6.0.

2-(Trimethylsilygl)ethyl-2,3,6-tri-O-benzoyl-4-O-(2,3,4,6-tetra-O-benzyl-α -D-galactopyranosyl)-β-D-galacopyranoside (L)

A solution of 2,3,4,6-tetra-O-benzyl-α,β-D-galactopyranosyl chloride (4.3 g, 7.7 mmol) in dry toluene (48 ml) was added, with exclusion of light and under nitrogen, to a solution of K (2.21 g, 3.73 mmol), silver trifluoromethanesulfonate (1.64 g, 6.38 mmol), tetramethylurea (0.90 ml, 7.50 mmol) and molecular sieves (4 Å, 2.7 g) in dry toluene (35 ml) at −40° C. The mixture was stirred at room temperature for 22 h, filtered and concentrated. Column chromatography (SiO$_2$, heptaneethyl acetate, 6:1) of the residue gave L (4.0 g, 96%), [α]$_D^{25}$=+56° (c=1.00, CDCl$_3$).

$^1$H-NMR data (CDCl$_3$): δ5.76 (dd, 1H, J 7.9 and 10.7 Hz, H-2), 5.22 (dd, 1H, J 3.1 and 10.7 Hz, H-3), 4.93 (d, 1H, J 3.5 Hz, H-1'), 4.86 (d, 1H, J 7.9 Hz, H-1), 4.21 (dd, 1H, J 2.7 and 10.2 Hz, H-3'), 3.62 (dt, 1H, J 6.5 and 10.2 Hz, OCH$_2$CH$_2$), 3.37 (brt, 1H, H-6'), 2.87 (dd, 1H, J 4.9 and 8.2 Hz, H-6'), 0.83–1.02 (m, 2H, CH$_2$CH$_2$Si), −0.08 (s, 9H, Si(CH$_3$)$_3$).

2-(Trimethylsilyl)ethyl-2,3,6-tri-O-benzoyl-4-O-(α-D-galactopyranosyl)-β -D-galactopyranoside (M)

A solution of L (1.95 g, 1.75 mmol) in acetic acid (20 ml) was hydrogenated (50 psi) over 10% Pd/C (447 mg) for 4 h 15 min. The mixture was filtered through celite and concentrated. Column chromatography of the residue (SiO$_2$, dichloromethane-methanol, 16:1) gave M (1.11 g, 85%), [α]$_D^{25}$=+71° (c=0.94, CDCl$_3$).

$^1$H-NMR data (CDCl$_3$): δ5.70 (dd, 1H, J 7.8 and 10.6 Hz, H-2), 5.21 (dd, 1H, J 2.9 and 10.6 Hz, H-3), 5.13 (d, 1H, J 3.7 Hz, H-1'), 4.84 (dd, 1H, J 6.6 and 11.4 Hz, H-6), 4.76 (d, 1H, J 7.8 Hz, H-1), 4.65 (dd, J 7,7 and 11.4 Hz, H-6), 4.49 (d, 1H, J 2.9 Hz, H-4), 3.62 (dt, 1H, J 6.6 and 9.9 Hz, OCH$_2$CH$_2$), 0.86–0.96 (m, 2H, CH$_2$CH$_2$Si), −0.08 (s, 9H, Si(CH$_3$)$_3$).

2-(Trimethylsilyl)ethyl-2,3,6-tri-O-benzoyl-4-O-(3-O-allyl-α-D-galactopyranosyl)-β -D-galactopyranoside (N)

A solution of M (734 mg, 0.973 mmol) in dry benzene (16 ml) was treated with dibutyltin oxide (290.6 mg, 1.17 mmol) and refluxed with azeotropic removal of water for 45 h (bath temperature 120° C.). Tetrabutylammoniumbromide (157 mg, 0.492 mmol) and allylbromide (1.60 ml, 18.5 mmol) were added, and the mixture was refluxed for another 8 h (bath temperature 90° C.). The mixture was concentrated and column chromatography (SiO$_2$, heptane-ethyl acetate, 1:1) of the residue gave N (594 mg, 77%), [α]$_D^{25}$=+81° (c=1.00, CDCl$_3$).

$^1$H-NMR data (CDCl$_3$): δ5.92–6.06 (m, 1H, CH$_2$CHCH$_2$), 5.70 (dd, 1H, J 7.8 and 10.6 Hz, H-2), 5.34–5.42 (m, 1H, CH$_2$CH—), 5.30 (dd, 1H, J 2.9 and 10.6 Hz, H-3), 5.24–5.30 (m, 1H, CH$_2$CH—), 5.09 (d, 1H, J 3.8 Hz, H-1'), 4.82 (dd, 1H, J 6.7 and 11.3 Hz, H-6), 4.77 (d, 1H, J 7.8 Hz, H-1), 4.71 (dd, 1H, J 7.6 and 11.3 Hz, H-6), 4.48 (d, 1H, J 2.9 Hz, H-4), 4.21–4.24 (m, 2H, —CHCH$_2$O—), 4.17 (dd, 1H, J 1.3 and 3.1 Hz, H-4'), 3.98 (dd, 1H, J 3.8 and 9.9 Hz, H-2'), 3.78 (dd, 1H, J 3.1 and 9.9 Hz, H-3'), 3.58–3.68 (dr, 1H, J 6.5 and 10.1 Hz, —OCH$_2$CH$_2$—), 3.29 (dd, 1H, J 3.9 and 11.9 Hz, H-6'), 3.21 (dd, 1H, J 5.2 and 11.9 Hz, H-6'), 0.82–1.02 (m, 2H, —CH$_2$CH$_2$Si), −0.07 (s, 9H, Si(CH$_3$)$_3$).

2-(Trimethylsilyl)ethyl-4-O-(3-O-allyl-α-D-galactopyranosyl)-β-D-galactopyranoside (O)

Compound N (577 mg, 0.69 mmol) was treated with methanolic sodium methoxide (0.57M, 1 ml) in methanol (50 ml) at room temperature for 20 h. The solution was neutralized with Duolite (H$^+$) resin, filtered and concentrated. Flash chromatography (SiO2, dichloromethane-ethanol, 5:1) of the residue gave 0 (331 mg, 99%), [α]$_D^{25}$=+77° (c=0.33, methanol).

$^{13}$C-NMR data (CD$_3$OD): δ138.2,118.9, 106.1, 104.1, 80.6, 80.4, 77.6, 76.3, 74.4, 74.1, 73.3, 71.5, 70.0, 69.6, 64.2, 62.5, 20.8, 0.2.

2-(Trimethylsilyl)ethyl-2,3,6-tri-O-benzyl-4-O-(3-O-allyl-2,4,6-tri-O-benzyl-α -D-galactopyranosyl)-β-D-galactopyranoside (P)

To a solution of 0 (172 mg, 0.36 mmol) in dry N,N-dimethylformamide (10 ml) was added sodium hydride in mineral oil (219 mg, 4.3 mmol, 50%) and benzylbromide (0.59 ml, 4.96 mmol). The mixture was stirred at room temperature for 2 h 15 min and methanol (7 ml) was added to destroy excess sodium hydride. The mixture was partitioned between dichloromethane and water, the aqueous layer was extracted with dichloromethane and the combined extract was washed with saturated aqueous sodium hydrogencarbonate and water, dried (Na$_2$SO$_4$), filtered and concentrated. Flash chromatography (SiO$_2$, heptane-ethyl acetate, 9:1) of the residue gave P (312 mg, 85%), [α]$_D^{25}$=+31° (c=1.01, CDCl$_3$).

$^1$H-NMR data (CDCl$_3$): δ7.15–7.39 (m, 30H, 6×C$_6$H$_5$—), 5.90–6.02 (m, 1H, CH$_2$CHCH$_2$—), 5.31–5.38 (m, 1H, CH$_2$CH—), 5.13–5.17 (m, 1H, CH$_2$CH—), 5.00 (d, 1H, J 3.4 Hz, H-1'), 4.32 (d, 1H, J 7.6 Hz, H-1), 1.02–1.08 (m, 2H, CH$_2$CH$_2$Si), 0.02 (s, 9H, S(CH$_3$)$_3$).

2-(Trimethylsilyl)ethyl-2,3,6-tri-O-benzyl-4-O-(2,4,6-tri-O-benzyl-α-D-galactopyranosyl)-β-D-galactopyranoside (Q)

A mixture of P (293 mg, 0.286 mmol) and palladium (II) chloride (29 mg) in methanol (4 ml) was stirred for 2 h at room temperature and then filtered through celite and concentrated. Flash chromatography (SiO$_2$, heptane-ethyl acetate, 7:1→5:1 gradient) of the residue gave Q (258 mg, 92%), [α]$_D^{25}$=+49° (c=0.99, CDCl$_3$).

$^1$H-NMR data (CDCl$_3$): δ5.09 (d, 1H, 3.2 Hz, H-1'), 4.33 d, 1H, J 7.5 Hz, H-1), 4.19 (dd, 1H, J 3.2 and 10.3 Hz, H-2'), 4.03 (d, 1H, J 2.9 Hz, H-4), 3.98 (brd, 1H, H-4'), 3.82 (dd, 1H, J 3.4 and 10.3 Hz, H-3'), 3.64 (dd, 1H, J 7.5 and 10.0 Hz, H-2), 3.39 (dd, 1H, J 2.9 and 10.0 Hz, H-3), 1.00–1.07 (m, 2H, CH$_2$CH$_2$Si), 0.01 (s, 9H, Si(CH$_3$)$_3$).

3,4,6-Tri-O-acetyl-2-deoxy-2-phthalimido-β-D-galactopyranosyl chloride

A solution of 1,3,4,6-tetra-O-acetyl-2-deoxy-2-phthalimido-α,β-D-galactopyranoside (506 mg, 1.06 mmol) in dry chloroform (1.7 ml) and α,α-dichloromethylmethyl ether (1.7 ml) was treated with borontrifluoride etherate (610 μl) for 19 h at room temperature. The mixture was diluted with dichloromethane, washed with ice-cold water and ice-cold, saturated, aqueous sodium hydrogencarbonate, dried (MgSO$_4$), filtered and concentrated to give a quantitative yield of the chloro sugar.

$^1$H-NMR data (CDCl$_3$): δ7.76–7.90 (m, 4H, C$_6$H$_4$), 6.17 (d, 1H, J 9.3 Hz, H-1), 5.80 (dd, 1H, J 3.4 and 11.2 Hz, H-3), 5.56 (brd, 1H, J 3.4 Hz, H-4), 4.74 (dd, 1H, J 9.3 and 11.2 Hz), 4.18–4.24 (m, 3H, H-5, H-6a and H-6b), 2.23, 2.08, 1.86 (3 s, 3H each, OAc).

2-(Trimethylsilyl)ethyl-2,3,6-tri-O-benzyl-4-O-(2,4,6-tri-O-benzyl-3-O-(3,4,6-tri-O-acetyl-2-deoxy-2-phthalimido-β-D-galactopyranosyl)-α-D-galactopyranosyl)-β-D-galactopyranoside (R)

A solution of 3,4,6-tri-O-acetyl-2-deoxy-2-phthalimido-β-D-galactopyranosyl chloride (480 mg, 1.06 mmol) in dry dichloromethane (6 ml) was added, with exclusion of light and under nitrogen, to a solution of Q (496 mg, 0.505 mmol), silver trifluoromethanesulfonate (517 mg, 2.0 mmol), sym-collidine (275 μl, 2.0 mmol) and molecular sieves (4 Å, 2.0 g) in dry dichloromethane (16 ml) at −78° C. The mixture was stirred at room temperature for 22 h, filtered and concentrated. Flash chromatography (SiO$_2$, heptane-ethyl acetate, 3:1) of the residue gave R (460 mg, 65%). Additional fractions of impure R (75 mg) were collected and starting material Q (58 mg, 12%) was regained, [α]$_D^{25}$=+21° (c=0.98, CDCl$_3$)

$^1$H-NMR data (CDCl$_3$): δ5.92 (dd, 1H, J 3.4 and 11.5 Hz, H-3"), 5.71 (d, 1H, J 8.3 Hz, H-1"), 5.53 (d, 1H, J 3.4 Hz, H-4"), 5.04 (d, 1H, J 11.2 Hz, PhCH$_2$—), 4.88 (d, 1H, J 11.0 Hz, PhCH$_2$—), 4.79 (d, 1H, J 3.4 Hz, H-1'), 4.73 (d, 1H, J 11.0 Hz, PhCH$_2$—), 4.66 (d, 1H, J 12.7 Hz, PhCH$_2$—), 4.66 (dd, J 8.3 and 11.5 Hz, H-2"), 4.62 (d, 1H, J 11.2 Hz, PhCH$_2$—), 4.46 (d, 1H, d 12.7 Hz, PhCH$_2$—), 4.29 (d, 1H, J 7.5 Hz, H-1.), 4.24 (d, 1.H, J 2.9 Hz, H-4), 3.84 (d, 1.H, J 3.0 Hz H-4'), 3.64 (dd, 1H, J 7.5 and 10.2 Hz, H-2), 3.32 (dd, 1H, J 2.9 and 10.2 Hz, H-3), 2.11, 1.97, 1.83 (3 s, 3H each, 3 OAc), 1.04–1.12 (m, 2H, CH$_2$CH$_2$Si), 0.04 (s, 9H, Si(CH$_3$)$_3$).

2-(Trimethylsilyl)ethyl 4-O-[3-O-(2-acetamido-2-deoxy-β-D-galactopyranosyl)-α-D-galactopyranosyl]-β-D-galactopyranoside (U)

Deprotection of compound R, followed by N-acetylation, can be performed in the usual way to give U. The acetylated derivatives S and T may be prepared in order to facilitate the interpretation of NMR spectra.

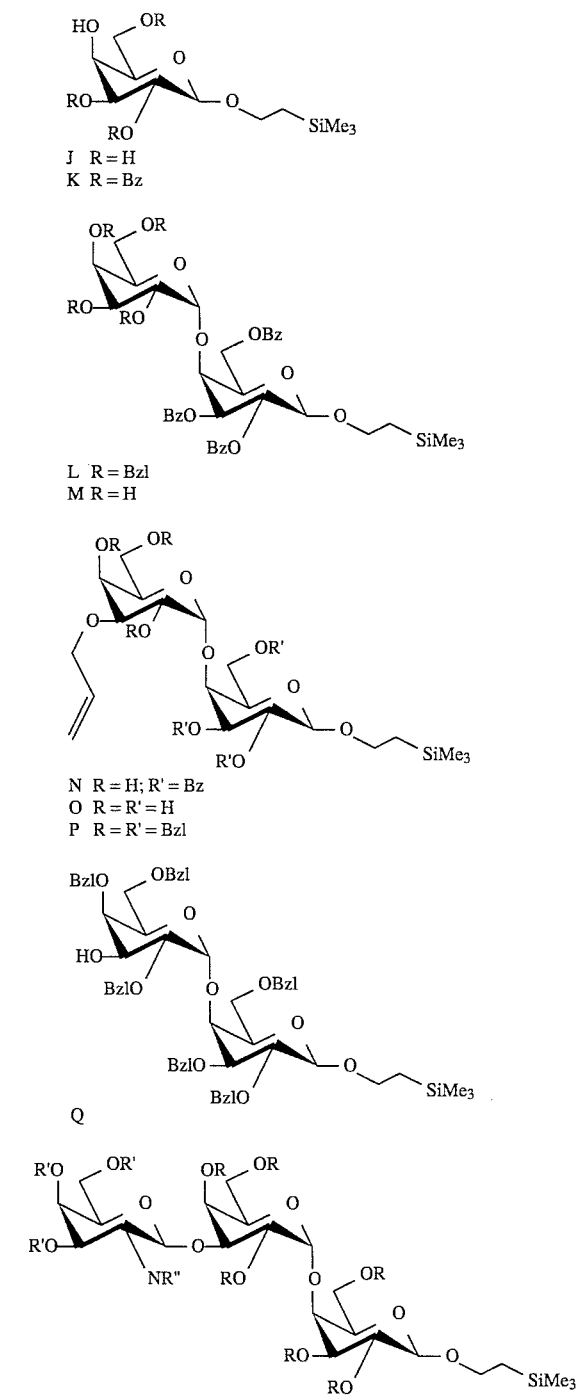

-continued

R  R = Bzl, R' = Ac, R" = Phth
S  R = R' = Ac, R" = Phth
T  R = R' = R" = Ac
U  R = R' = H, R" = H, Ac

EXAMPLE 5

2-(Trimethylsilyl)ethyl 3-O-allyl-β-D-galactopyranoside (V)

A solution of compound J (649 mg, 2.32 mmol) in dry benzene (40 ml) was treated with dibutyltin oxide (693 mg, 2.80 mmol) and refluxed with azeotropic removal of water for 24 h 30 min (oil bath temperature 110° C.). Tetrabutylammonium bromide (373 mg, 1.16 mmol) and allylbromide (3.82 ml, 44.2 mmol) were added and the mixture was refluxed for another 3 h (oil bath temperature 90° C.). The mixture was concentrated and column chromatography ($SiO_2$, heptane-ethyl acetate, 1:2) of the residue gave V (517 mg, 70%), $[\alpha]_D^{25}=-8.5°$ (c=0.96, $CDCl_3$).

$^1$H-NMR data ($CDCl_3$): δ5.89–6.03 (m, 1H, $CH_2CHCH_2$—), 5.21–5.38 (m, 2H, $CH_2$—CH—), 4.28 (d, 1H, J 7.8 Hz, H-1), 4.19–4.24 (m, 2H, $CHCH_2O$—), 3.55–3.65 (m, 1H, —$OCH_2CH_2$—), 3.52 (brt, 1H, H-5), 3.40 (dd, 1H, J 3.4 and 9.5 Hz, H-3), 0.92–1.11 (m, 2H, $CH_2CH_2Si$), 0.02 (s, 9H, $Si(CH_3)_3$).

2-Trimethylsilyl)ethyl-3-O-allyl-2,4,6-tri-O-benzyl-β-D-galactopyranoside (X)

To a solution of V (507 mg, 1.58 mmol) in dry N,N-dimethylformamide (10.6 ml) was added sodium hydride (0.31 g, 6.33 mmol, 50%) and benzylbromide (1.31 ml, 11.0 mmol). The mixture was stirred at room temperature for 18 h and methanol (10 ml) was added to destroy excess sodium hydride. The mixture was partitioned between ethyl acetate and water, and the organic layer was washed twice with water, dried ($Na_2SO_4$), filtered and concentrated. Column chromatography ($SiO_2$, toluene) of the residue gave X (859 mg, 92%), $[\alpha]_D^{25}=-13°$ (c=1, $CDCl_3$).

$^1$H-NMR data ($CDCl_3$): δ5.86–6.01 (m, 1H, $CH_2CHCH_2$—), 5.32 (br dd, 1H, $CH_2CH$—), 5.17 (br dd, 1H, $CH_2CH$—), 4.93 (d, 1H, J 11.8 Hz, $PhCH_2$), 4.91 (d, 1H, J 11.0 Hz, $PhCH_2$), 4.76 (d, 1H, J 11.0 Hz, $PhCH_2$), 4.60 (d, 1H, J 11.8 Hz, $PhCH_2$), 4.47 (d, 1H, J 11.75 Hz, $PhCH_2$), 4.41 (d, 1H, J 11.75 Hz, $PhCH_2$), 4.35 (d, 1H, J 7.7 Hz, H-1), 4.17–4.22 (m, 2H, —$CHCH_2O$—), 4.00 (dr, 1H, J 8.4 and 9.4 Hz, $OCH_2CH_2$), 3.86 (d, 1H, J 2.9 Hz, H-4), 3.74 (dd, 1H, J 7.7 and 9.7 Hz, H-2), 3.42 (dd, 1H, d 2.9 and 9.7 Hz, H-3), 1.03 (m, 2H, $CH_2CH_2Si$), 0.15 (s, 9H, $Si(CH_3)_3$).

Anal. Calc. for $C_{35}H_{46}O_6Si$: C, 71.1; H, 7.8. Found: C, 69.7; H, 7.7.

3-O-allyl-2,4,6-tri-O-benzyl-D-galactopyranose (Y)

Compound X (842 mg, 1.43 mmol) was dissolved in dichloromethane (7.2 ml) under nitrogen, trifluoroacetic acid (14.3 ml) was added at 0° C., and the mixture was stirred at 0° C. for 25 minutes. n-Propylacetate (43 ml) and toluene (87 ml) were added and then removed at about 6 Torr. A second portion of toluene (57 ml) was added and removed. Column chromatography ($SiO_2$, heptane-ethyl acetate, 2:1) of the residue gave Y (625 mg, 89%).

$^1$H-NMR data ($CDCl_3$): δ5.84–6.02 (m, 1H, $CH_2CHCH_2$—), 5.17–5.39 (m, 2H, $CH_2CH$—), 5.26 (brd, 1H, H-α1), 4.63 (brd, 1H, H-1β), 3.98 (dd, 1H, d 3.6 and 9.8 Hz, H-2α), 3.94 (brd, 1H, H-4α), 3.87 (brd, 1H, H-4β), 3.80 (dd, 1H, J 2.8 and 9.8 Hz, H-3α), 3.70 (dd, 1H, J 7.4 and 9.7 Hz, H-2β), 3.44 (dd, 1H, d 2.9 and 9.7 Hz, H-3β).

Anal. Calc. for $C_{30}H_{34}O_6$: C, 73.4; H, 7.0. Found: C, 73.3; H, 7.2.

3-O-allyl-2,4,6-tri-O-benzyl-D-galactopyranosyl chloride (Z)

Compound Y (505 mg, 1.03 mmol) in dry dichloromethane (8 ml) was treated with N,N-dimethylformamide (0.55 ml) and oxalyl chloride (0.55 ml) at room temperature for 45 minutes. The mixture was diluted with ice-cold toluene (40 ml), then quickly washed with ice-cold water (6 ml) and ice-cold, saturated, aqueous sodium hydrogencarbonate (6 ml), dried ($Na_2SO_4$) and concentrated to give crude Z in quantitative yield.

2-(Trimethylsilyl)ethyl-2,3,6-tri-O-benzoyl-4-O-(3-O-allyl-2,4,6 -tri-O-benzyl-α-D-galactopyranosyl)-β-D-galactopyranoside (ZA)

A solution of crude Z (520 mg, 1.02 mmol) in dry toluene (11 ml) was added, with exclusion of light and under nitrogen, to a solution of K (509 mg, 0.859 mmol), silver trifluoromethanesulfonate (449 mg, 1.75 mmol), tetramethylurea (207 μl, 1.75 mmol) and molecular sieves (4 Å, 0.6 g) in dry toluene (8 ml) at −45° C. The mixture was stirred at room temperature for 19 h, filtered and concentrated. Repeated column chromatography ($SiO_2$, heptane-ethyl acetate, 7:1, then 3:1) of the residue gave ZA (698 mg, 75%), $[\alpha]_D^{25}=+47°$ (c=1, $CHCl_3$).

$^1$H-NMR data ($CDCl_3$): δ5.92–6.06 (m, 1H, $CH_2CHCH_2$—), 5.73 (dd, 1H, J 7.8 and 10.6 Hz H-2), 5.39 (m, 1H, $CH_2CH$—), 5.20 (m, 1H, $CH_2CH$—), 5.20 (dd, 1H, J 3.5 and 10.6 Hz, H-3), 4.71 (d, 1H, J 7.8 Hz, H-1), 3.61 (dt, 1H, J 6.6 and 10.0 Hz, —$OCH_2CH_2$—), 0.82–1.02 (m, 2H, —$CH_2CH_2Si$—), −0.08 (s, 9H, $Si(CH_3)_3$).

Anal. Calc. for $C_{62}H_{68}O_{14}Si$: C, 69.9; H, 6.4. Found: C, 68.8; H, 6.4.

2-(Trimethylsilyl)ethyl-2,3,6-tri-O-benzoyl-4-O-(3-O-propyl-α -D-galactopyranosyl)-β-D-galactopyranoside (ZB)

Compound ZA (211 mg, 0.198 mmol) was hydrogenated at atmospheric pressure in acetic acid over 10% Pd/C for 7 h. The mixture was filtered through celite and concentrated. Column chromatography ($SiO_2$, heptane-ethyl acetate, 1:3) of the residue gave ZB (113 mg, 72%), $[\alpha]_D^{25}=+84°$ (c=1, $CDCl_3$).

$^1$H-NMR data ($CDCl_3$): δ5.71 (dd, 1H, J 7.7 and 10.6 Hz, H-2), 5.30 (dd, 1H, J 2.9 and 10.6 Hz, H-3), 5.09 (d, 1H, J 3.7 Hz, H-1'), 4.83 (dd, 1H, J 6.6 and 11.2 Hz, H-6), 4.77 (d, 1H, J 7.7 Hz, H-1), 4.73 (dd, 1H, J 7.5 and 11.2 hz, H-6), 4.48 (d, 1H, J 2.9 Hz, H-4), 4.18 (brd, 1H, H-4'), 4.11 (brt, 1H, H-5), 3.70 (dd, 1H, J 3.1 and 9.9 Hz, H-3'), 1.68 (m, 2H, $CH_3CH_2CH_2$—), 0.97 (t, 3H, J 7.3 Hz, —$CH_2CH_3$), 0.82–1.02 (m, 2H, —$CH_2CH_2Si$), −0.07 (s, 9H, $Si(CH_3)_3$).

Anal. Calc. for $C_{41}H_{52}O_{14}Si$: C, 61.8; H, 6.6. Found: C, 61.4; H, 6.6.

2-(Trimethylsilyl)ethyl-4-O-(3-O-propyl-α-D-galactopyranosyl)-β -D-galactopyranoside (ZC)

A solution of ZB (67.0 mg, 0.082 mmol) in methanol (11 ml) was treated with methanolic sodium methoxide (0.57M, 150 μl) for 7 h. The mixture was neutralized with Duolite ($H^+$) resin, filtered and concentrated. Column chromatography ($SiO_2$, dichloromethane-ethanol, 4:1) of the residue gave ZC (38 mg, 95%), $[\alpha]_D^{25}=+77°$ (c=1.1, $Me_2SO-d_6$).

$^1$H-NMR data (Me2SO-$d_6$): δ4.81 (d, 1H, J 3.6 Hz, H-1'), 4.12 (d, 1H, J 7.4 Hz, H-1), 1.54 (m, 2H, —$CH_2CH_2CH_3$), 0.89 (t, 3H, J 7.4 Hz, —$CH_2CH_3$), 0.81–1.02 (m, 2H, $CH_2CH_2Si$), 0.01 (s, 9H, $Si(CH_3)_3$).

$^{13}$C-NMR data (Me2SO-$d_6$): δ102.9, 100.4, 77.8, 77.1, 74.3, 73.1, 71.0, 70.8, 70.0, 67.5, 65.6, 65.1, 60.2, 59.2, 22.7, 17.8, 10.5, −1.4.

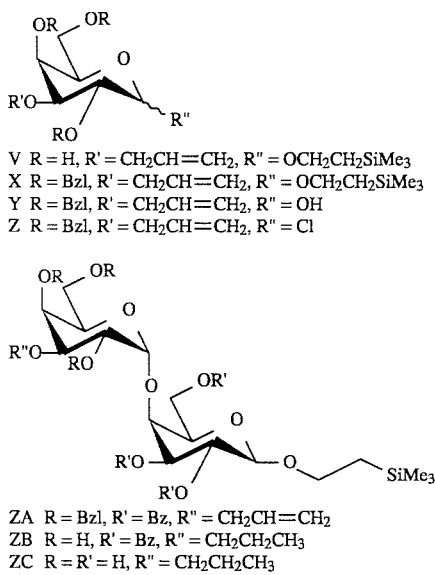

V  R = H, R' = CH₂CH=CH₂, R" = OCH₂CH₂SiMe₃
X  R = Bzl, R' = CH₂CH=CH₂, R" = OCH₂CH₂SiMe₃
Y  R = Bzl, R' = CH₂CH=CH₂, R" = OH
Z  R = Bzl, R' = CH₂CH=CH₂, R" = Cl

ZA  R = Bzl, R' = Bz, R" = CH₂CH=CH₂
ZB  R = H, R' = Bz, R" = CH₂CH₂CH₃
ZC  R = R' = H, R" = CH₂CH₂CH₃

EXAMPLE 6

Test of inhibition of haemagglutination

Bacterial strain HB101/pPAP5. Plasmid pPAP5 carries the pap gene cluster isolated from the uropathogenic *E.coli* isolate J96. The clone produces P pili that mediate agglutination of human erythrocytes by binding to the galabiose-containing P-blood group antigens present on the erythrocyte surface. The galabiose binding property resides in the PapG gene product which is present at the tip of the P pilus as a minor component.

Haemagglutination (HA) reactions

HA of a 1% human P erythrocyte suspension in phosphate-buffered saline was determined for agar-grown organisms by suspending the bacteria to a Klett of 490 (ca 1×10⁹ bacteria/mL). A sample of the bacterial suspension (25 µL) was serially diluted in microtiter plates containing 25 µL PBS in each well. An equal volume of erythrocyte suspension was added and after mixing, the plates were incubated at 4° C. for 18 h. The HA endpoint was defined as the dilution in the last well before erythrocyte buttons were formed. The titer was expressed as the reciprocal of the endpoint dilution.

HA inhibition

The HA titer of the strains to be tested was determined as described above and the cells were diluted so that each strain gave a titer of 64. The concentration of each of the analogues 1–25 was adjusted to 100 mM and 25 µL of each analogue was serially diluted in microtiter plates containing 25 µL of PBS in each well. The bacterial suspension (25 µL; HA titer=64) was then added to each well. After incubation for 30 min at room temperature, human erythrocytes (1% suspension) were added by gentle mixing and the plates were incubated at 4° C. overnight. The endpoint was defined as the greatest dilution of the analogue (minimal concentration) that gave a 50% inhibition of the HA ($IC_{50}$).

For the compounds 1–25, tables 1 and 2 below show the experimentally determined $IC_{50}$ values and the relative potency in percent in relation to compound 1 calculated therefrom as well as the calculated $\Delta\Delta G°$ for the bonding. Scheme I shows in a condensed form for each compound partly the relative potency in relation to compound 1 and partly the nature of the modification carried out in the indicated position. The scheme is to be understood, as it will also be evident from the tables, that for each compound, the modification indicated in the various boxes was carried out in the indicated position, the molecule otherwise being unmodified, i.e. that all the other positions were unchanged in relation to the parent galabioside.

The $IC_{50}$-values given in the tables are mean values from 3 consecutive runs. The ratio of the $IC_{50}$-value for an inhibitor and compound 1 is the relative equilibrium constant, $K_{rel}$. This value was used for the calculation of the difference free energy values ($\Delta\Delta G°$) using the expression $\Delta\Delta G°=RT\ln K_{rel}$. It should be stressed that the conclusions made here about the nature of the adhesin receptor is based on the assumption that all the inhibitors have similar over-all confirmations oriented in a similar way in the receptor side and that only one type of galablest-specific receptor is present in the adhesin. Furthermore, it is assumed that any metal ions present in the buffers used in the agglutination did not have any marked influence on the protein-sugar binding in analogy with what has been established previously.

From table 1 it is apparent that modification of the 3'-position by introducing a methyl group on the oxygen atom (cf. compound 11) produces a marked increase in the inhibitory power of the methyl galabioside whereas the various modifications conducted in the other positions results in either a clear reduction of the inhibitory power or causes the inhibitory power to disappear almost completely. These results therefore strongly indicate that compounds of the invention will constitute improved bacteria-binding galabiosides of potential value for diagnosis and therapy of urinary tract infection.

With respect to compounds 18–26 which were modified in the anomeric position, it is clear that the aglycon must first of all be present in the β-form, (cf. compound 23) and that increased lipophilicity causes a marked increase in inhibitory power in the otherwise unmodified galabioside. In particular, the dimeric compound 25 displayed very high inhibitory power. These results indicate that aglycon moieties of the type indicated in formula I will further enhance the increases in inhibitory power obtained through the modifications in the 3'-position defined in formula I.

TABLE 1

Inhibition by Galα1-4GalβOMe(1) and analogues of the agglutination of human erythrocytes by *E. coli*

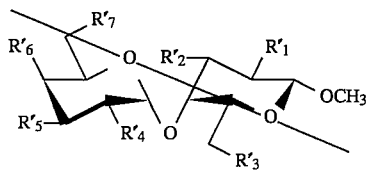

| Compound | R'$_1$ | R'$_2$ | R'$_3$ | R'$_4$ | R'$_5$ | R'$_6$ | R'$_7$ | IC$_{50}$ (mM) | Relative potency (%) | ΔΔG° (kJ mol$^{-1}$) |
|---|---|---|---|---|---|---|---|---|---|---|
| 1 | OH | OH | OH | OH | OH | OH | OH | 0.20 | 100 | 0.0 |
| 2 | H | OH | OH | OH | OH | OH | OH | 0.35 | 56 | 1.4 |
| 3 | OH | H | OH | OH | OH | OH | OH | 1.0 | 19 | 3.9 |
| 4 | OH | OH | H | OH | OH | OH | OH | 4.2 | 4.7 | 7.1 |
| 5 | OH | OH | OH | H | OH | OH | OH | 2.6 | 7.6 | 6.0 |
| 6 | OH | OH | OH | OH | H | OH | OH | 6.5 | 3.0 | 8.2 |
| 7 | OH | OH | OH | OH | OH | H | OH | 10 | 1.9 | 9.2 |
| 8 | OH | OH | OH | OH | OH | OH | H | 3.7 | 5.3 | 6.8 |
| 9 | OH | OMe | OH | OH | OH | OH | OH | 1.6 | 12 | 4.9 |
| 10 | OH | OH | OMe | OH | OH | OH | OH | >25 | <1 | >11 |
| 11 | OH | OH | OH | OH | OMe | OH | OH | 0.087 | 220 | −1.8 |
| 12 | OH | OH | F | OH | OH | OH | OH | 9.3 | 2.1 | 9.0 |
| 13 | OH | OH | OH | OH | OH | F | OH | 3.5 | 5.6 | 6.7 |
| 14 | OH | OH | OH | OH | OH | OH | F | 0.35 | 56 | 1.35 |
| 15 | OH | Me | OH | OH | OH | OH | OH | 0.39 | 50 | 1.6 |
| 16 | OH | Et | OH | OH | OH | OH | OH | 3.8 | 5.1 | 6.9 |
| 17 | OH | OH | OH | OH | OH | epi | OH | 5.1 | 3.8 | 7.6 |

TABLE 2

Inhibition by Galα1-4GalβOMe (1) and glycoside analogs of the agglutination of human erythrocytes by *E. coli*.

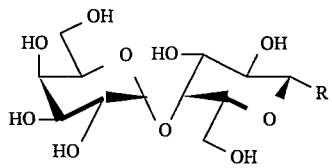

| Cmpd | R | IC$_{50}$ (mM) | Inhib. power (%) | ΔΔG (kJmol$^{-1}$) |
|---|---|---|---|---|
| 1 | OCH$_3$ | 0.20 | 100 | 0.00 |
| 18 | OCH$_2$CH$_3$ | 0.13 | 150 | −0.9 |
| 19 | OCH$_2$CH(CH$_3$)$_2$ | 0.087 | 220 | −1.8 |
| 20 | OCH$_2$CH$_2$Si(CH$_3$)$_3$ | 0.049 | 400 | −3.2 |
| 21 | OCH$_2$CH(OH)CH$_2$OH | 0.13 | 150 | −0.9 |
| 22 | O-4GlcβOCH$_2$CH$_2$Si(CH$_3$)$_3$ | 0.26 | 75 | 0.7 |
| 23 | αOMe | 2.1 | 9.0 | 5.6 |
| 24 | αβOH | 1.4 | 14 | 4.6 |
| 25 | Galα1-4GalβO(CH$_2$)$_2$S(CH$_2$)$_9$—S(CH$_2$)$_2$O | 0.0068 | 2900 | −7.8 |
| 26 | Galβ1-4GlcβOCH$_2$CH$_3$ | >25 | <1.0 | >11 |
| 27[a] | OCH$_2$CH[CH$_2$SO$_2$(CH$_2$)$_3$CH$_3$]$_2$ | 0.0023 | 1887 | −6.8 |
| 28[a] | SCH$_2$CH$_3$ | 0.0163 | 266 | −2.3 |

[a]separate inhibition experiment where the reference compound 1 showed IC$_{50}$ = 0.0434 mM.

Scheme 1.
Relative inhibitory power of galabiose analogs

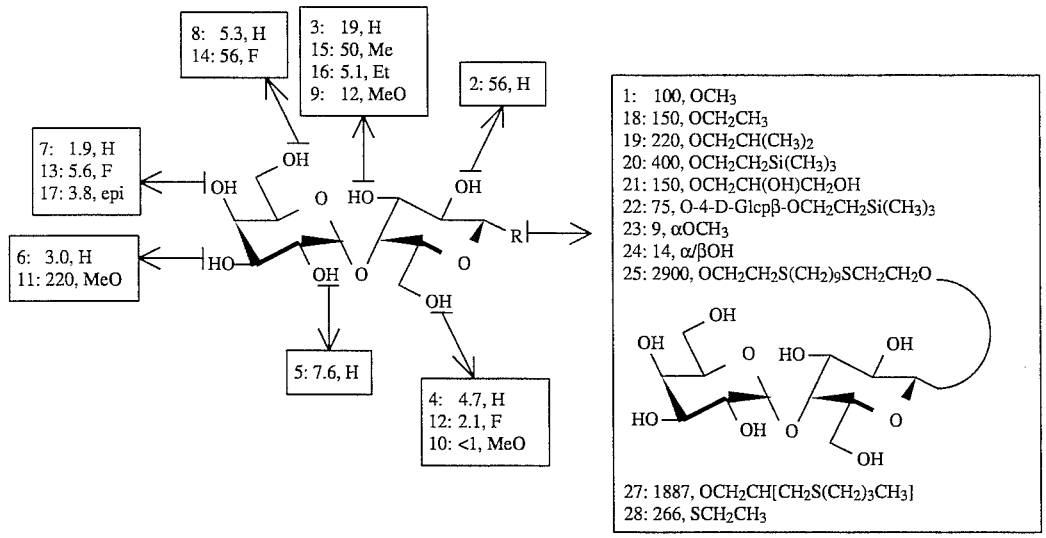

We claim:

1. Compounds of the formula I

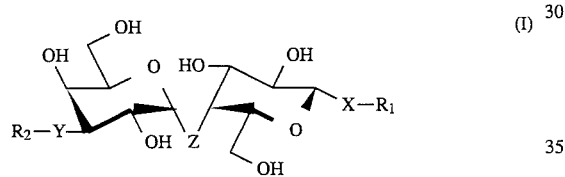

wherein (a) $R_1$ is selected from the group consisting of
  (i) $C_{1-24}$ alkyl;
  (ii) $C_{2-24}$ alkenyl;
  (iii) $C_{2-24}$ alkynyl;
  (iv) tri($C_{1-4}$ alkyl)silylethyl;
  (v) aryl;
  (vi) mono- and di-halogen-$C_{1-4}$ alkyl;
  (vii) aryl substituted with a substituent selected from the group consisting of hydroxy, amino, $C_{1-4}$ alkyl, $C_{1-4}$ alkoxy, nitro, halogen, and phenoxy;
  (viii) $R_3$—$(CH_2)_n$—S—$CH_2CH_2$—
  (ix) ($R_3$—$(CH_2)_n$—S—$CH_2)_2CHCH_2$—
  (x) $R_3$—$(CH_2)_n$—$SO_2$—$CH_2CH_2$—
  (xi) ($R_3$—$(CH_2)_n$—$SO_2$—$CH_2)_2CHCH_2$—
    wherein $R_3$ is selected from the group consisting of H, —COOH, —COO—$C_{1-4}$ alkyl, hydroxy, amino, and an inorganic, polymeric or macromolecular carrier, and n is an integer from 1 to 24;
  (xii) $Z^1$—S—$CH_2$—$CH_2$—
  (xiii) ($Z^1$—S—$CH_2)_2CHCH_2$—
  (xiv) $Z^1$—$SO_2$—$CH_2$—$CH_2$—
  (xv) ($Z^1$—$SO_2$—$CH_2)_2CHCH_2$—
    wherein each $Z^1$ is selected from the group consisting of phenyl and phenyl monosubstituted with hydroxy, amino, $C_{1-4}$ alkyl, $C_{1-4}$ alkoxy, nitro, halogen, or phenoxy;
  (xvi) $R_4CH_2CH(CH_2R_5)CH_2$—
    wherein $R_4$ and $R_5$ independently are halogen; and
  (xvii) Q—$(CH_2)_n$— wherein Q is an inorganic, polymeric or macromolecular carrier, and n is an integer from 1 to 24;

(b) $R_2$ is selected from the group consisting of glycosidically connected monosaccharide; glycosidically connected disaccharide; $C_{1-18}$ alkyl; $C_{2-18}$ alkenyl; $C_{2-18}$ alkynyl; $C_{1-18}$ alkyloxymethyl; $C_{1-18}$ alkanoyl; α-hydroxy-$C_{1-18}$ alkanoyl; naphthyl-, heterocyclyl- or phenyl-$C_{1-18}$ alkoxy; naphthyl-$C_{1-8}$ alkoxy, heterocyclyl-$C_{1-8}$ alkoxy, or phenyl-$C_{1-18}$ alkoxy where the naphthyl, heterocyclyl or phenyl group is substituted with hydroxyl, amino, $C_{1-4}$ alkyl, $C_{1-4}$ alkoxy, nitro, halogen, or phenoxy; tri($C_{1-4}$-alkyl)silylethyl; tri($C_{1-4}$-alkyl)silyl; tri($C_{1-4}$-alkyl)silylethoxymethyl; halogen; ω-hydroxy-$C_{1-4}$-alkyl; tetrahydropyranyl; benzyloxymethyl; $C_{3-8}$ cycloalkyl; monoterpenyl; benzoyl; and benzoyl monosubstituted with hydroxyl, amino, $C_{1-4}$ alkyl, $C_{1-4}$ alkoxy, nitro, halogen, or phenoxy; the acyl residue of a naturally occurring amino acid; and

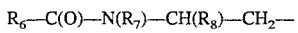

wherein $R_6$ is $C_{1-4}$ alkyl; phenyl; and phenyl substituted with a substituent selected from the group consisting of hydroxyl, amino, $C_{1-4}$ alkyl, $C_{1-4}$ alkoxy, nitro, halogen, and phenoxy;
$R_7$ is H or $C_{1-4}$ alkyl; and
$R_8$ is H, $C_{1-4}$ alkyl, or hydroxy-$C_{1-4}$ alkyl;

(c) Z is —O—, —S—, —$SO_2$—, or —$CH_2$—;

(d) X is —O—, —S—, —$SO_2$—, —$CH_2$—, or —$NR_{10}$—, wherein $R_{10}$ is H or $R_2$ above, and $R_{10}$ in X and $R_1$ are optionally connected to form a ring; and (e) Y is —O— or —$NR_{11}$— wherein $R_{11}$ is H or $R_2$ above, and $R_{11}$ in X and $R_2$ are optionally connected to form a ring.

2. A compound of claim 1 wherein Z is —O—.
3. A compound of claim 1 wherein Y is —O—.
4. A compound of claim 1 wherein X is —O— or —S—.
5. A compound of claim 1 wherein $R_2$ and Y together is ($C_{1-8}$ alkyl)$_2$N— where the two $C_{1-8}$ alkyl groups optionally are connected to form a ring.
6. A compound of claim 1 wherein $R_1$ is selected from the group consisting of $C_{1-24}$ alkyl; tri($C_{1-4}$ alkyl)silylethyl; aryl; aryl substituted with amino or nitro; $R_3$—$(CH_2)_n$—S—$CH_2CH_2$—, ($R_3$—$(CH_2)_n$—S—$CH_2)_2CHCH_2$—, $R_3$—$(CH_2)_n$—$SO_2$— $CH_2CH_2$—, or $(R_3$—$(CH_2)_n$—$SO_2$—$CH_2)_2CHCH_2$— wherein $R_3$ is H, —COOH, —COO—$C_{1-4}$ alkyl, or an inorganic, polymeric, or macromolecular carrier, and n is as defined; $Z^1$—S—$CH_2$—$CH_2$—, $(Z^1$—S—$CH_2)_2CHCH_2$—, $Z^1$—$SO_2$—$CH_2$—$CH_2$—, or $(Z^1$—$SO_2$—$CH_2)_2CHCH_2$—, wherein each $Z^1$ is phenyl or is phenyl monosubstituted with amino or nitro; and a group Q—$(CH_2)_n$— wherein Q is an inorganic, polymeric or macromolecular carrier and n is an integer from 1 to 24.

7. A compound of claim 1 wherein $R_2$ is selected from the group consisting of glycosidically connected monosaccharide; glycosidically connected disaccharide; $C_{1-18}$ alkyl; $C_{2-18}$ alkenyl; $C_{1-18}$ alkyloxymethyl; tetrahydropyranyl; and benzyloxymethyl.

8. A compound of claim 1 wherein $R_2$ is selected from the group consisting of 2-acetamido-2-deoxy-β-D-galactopyranosyl; 2-deoxy-2-phthalamido-β-D-galactopyranosyl; 2-D-galactopyranosyl; $C_{1-6}$ alkyl; $C_{1-6}$ alkyloxymethyl; tetrahydropyranyl; and benzyloxymethyl.

9. A compound of claim 1 wherein —$XR_1$ is selected from the group consisting of —S—$CH_2CH_3$, —O—$CH_2CH\{CH_2SO_2(CH_2)_3CH_3\}_2$, —S—$CH_2CH\{CH_2SO_2(CH_2)_3CH_3\}_2$, and —$CH_2$—$CH_2CH\{CH_2S(CH_2)_3CH_3\}_2$.

10. A compound of the formula VI:

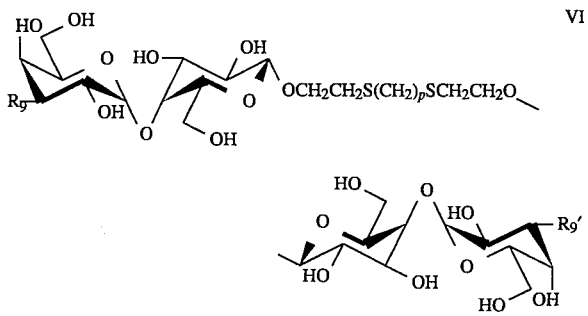

where $R_9$ and $R_9'$ independently are selected from the group consisting of —OH, $CH_3O$—, $CH_3CH_2O$— and $(CH_3)_2CHO$—, and p is an integer from 1 to 12.

11. A compound of claim 1 which is GalNAcβO-galabiose-$O(CH_2)_2Si(CH_3)_3$.

12. A compound of claim 1 which is GalβO-galabiose-$O(CH_2)_2Si(CH_3)_3$.

13. A compound of claim 1 which is $CH_3$—O-galabiose-$O(CH_2)_2Si(CH_3)_3$.

14. A compound of claim 1 which is $CH_3CH_2O$-galabiose-$O(CH_2)_2Si(CH_3)_3$.

15. A compound of claim 1 which is $CH_2$=$CHCH_2O$-galabiose-$O(CH_2)_2Si(CH_3)_3$.

16. A compound of claim 1 wherein $R_2$ is methyl.

17. A compound of claim 1 wherein $R_1$ is selected from the group consisting of ethyl, isopropyl, trimethylsilylethyl, —$CH_2CH(OH)CH_2OH$, and —$CH_2CH\{CH_2S(CH_{23}CH_3\}_2$.

18. A compound of claim 1 wherein X, Y and Z are —O— and $R_1$ is $CH_2CH\{CH_2S(CH_2)_3CH_3\}_2$.

19. A compound of claim 1 in which $R_1$ is tri($C_{1-4}$ alkyl)silylethyl.

20. A compound of claim 10 in which $R_9$ and $R_9'$ are both —OH and p=9.

21. A pharmaceutical composition comprising at least one compound of formula I as defined in claim 1 and a pharmaceutically acceptable excipient.

22. A method for treating or reducing the incidence of infections caused by galabiose-binding bacteria in a patient comprising administering to said patient an effective amount of a compound as claimed in claim 1 to treat or reduce the incidence of said bacterial infection.

23. The method of claim 22 wherein said compound is administered by a method selected from the group consisting of oral administration, intravenous injection, and aerosol administration.

24. The method of claim 22 wherein the compound is selected from the group consisting of
GalNAcβO-galabiose-O—$(CH_2)_2Si(CH_3)_3$,
GalβO-galabiose-$O(CH_2)_2Si(CH_3)_3$,
$CH_3O$-galabiose-$O(CH_2)_2Si(CH_3)_3$,
$CH_3CH_2O$-galabiose-$O(CH_2)_2Si(CH_3)_3$, and
$CH_2$=$CHCH_2O$-galabiose-$O(CH_2)_2Si(CH_3)_3$.

25. The method of claim 22 wherein $R_2$ is methyl.

26. The method of claim 22 wherein $R_1$ is selected from the group consisting of ethyl, isopropyl, trimethylsilylethyl, —$CH_2CH(OH)_2CH_2OH$, and —$CH_2CH\{CH_2S(CH_2)_3CH_3\}_2$.

27. The method of claim 22 wherein X, Y and Z are —O— and $R_1$ is —$CH_2CH\{CH_2S(CH_2)_3CH_3\}_2$.

28. The method of claim 22 wherein $R_1$ is tri($C_{1-4}$ alkyl)silylethyl.

29. The method of claim 22 wherein the compound has the formula:

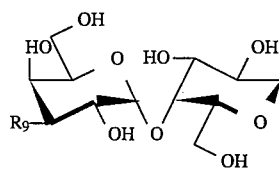 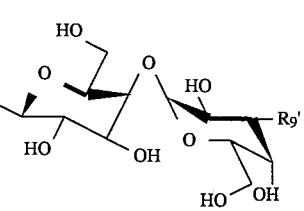

where $R_9$ and $R_9'$ independently are selected from the group consisting of —OH, $CH_3O$—, $CH_3CH_2O$— and $(CH_3)_2CHO$—, and p is an integer from 1 to 12.

30. The method of claim 29 wherein $R_9$ and $R_9'$ are both —OH and p=9.

31. The method of claim 22 wherein the bacterial infections are uropathogenic *E. coli* infections.

* * * * *